United States Patent [19]

Bavoil et al.

[11] Patent Number: 5,741,697
[45] Date of Patent: Apr. 21, 1998

[54] BACTERIOPHAGE OF *CHLAMYDIA PSITTACI*

[75] Inventors: Patrik M. Bavoil; Ru-Ching Hsia, both of Pittsford, N.Y.

[73] Assignee: University of Rochester, Rochester, N.Y.

[21] Appl. No.: 565,386

[22] Filed: Nov. 30, 1995

[51] Int. Cl.$^6$ .............................. C12N 7/00; C07H 21/04
[52] U.S. Cl. .................... 435/235.1; 435/320.1; 530/388.3; 536/23.72; 536/24.3
[58] Field of Search ................ 435/235.1, 320.1; 530/388.3; 536/23.72, 24.3

[56] References Cited

U.S. PATENT DOCUMENTS

| | | | |
|---|---|---|---|
| 4,703,009 | 10/1987 | MacNeil et al. | 435/172.3 |
| 4,822,738 | 4/1989 | Miwa et al. | 435/252.3 |
| 4,828,999 | 5/1989 | Jackson | 435/235 |
| 4,865,979 | 9/1989 | Nakano et al. | 435/172.3 |
| 5,132,221 | 7/1992 | Ward et al. | 435/235.1 |

FOREIGN PATENT DOCUMENTS

WO 89/00695  1/1989  WIPO ...................... G01N 33/569

OTHER PUBLICATIONS

Richmond et al., "Virus Infecting the Reticulate Bodies of an Avian Strain of *Chlamydia Psittaci*," *FEMS Microbiology Letters*, 14:31–36 (1982).

Storey et al., "Analysis of the Complete Nucleotide Sequence of Chp 1, a Phage Which Infects Avian *Chlamydia Psittaci*," *J. Gen Virol.*, 70:3381–3390 (1989).

*Primary Examiner*—Ponnathapura Achutamurthy
*Assistant Examiner*—Phuong T. Bui
*Attorney, Agent, or Firm*—Nixon, Hargrave, Devans & Doyle LLP

[57] ABSTRACT

The present invention is directed to an isolated bacteriophage designated φCPG1. The invention is further directed to an isolated DNA molecule encoding bacteriophage φCPG1, or a fragment thereof, a DNA molecule comprising DNA encoding bacteriophage φCPG1 with heterologous DNA inserted therein, or a fragment thereof, and to oligonucleotides consisting essentially of a portion of the DNA molecule encoding φCPG1. The bacteriophage φCPG1 was isolated from *Chlamydia psittaci* strain Guinea Pig inclusion Conjunctivitis.

13 Claims, 4 Drawing Sheets

```
phiCPG1 SEQ. ID NO:2:        156 ATGGTTAGGAATCGGCGTTTG          176
                                 |||||| ||  ||          |
Chp1    SEQ. ID NO:10:      4460 ATGGCTAAAGGACGAAAGCTT         4480

177 CCTTCAGTTATGAGTCATTCTTTCGCGCAAGTGCCATCAGCGCGAATTCA    226
    || | |||||||  ||  ||| | ||| ||  ||||       |   |||
4481 CCGTCGGTTATGAAGAATCGTTTTTCAGAGGTACCGACAGCTACGATTAG   4530

227 GAGAAGTTCTTTTGATAGATCTTGTGGTTTAAAGACTACATTCGACGCCG    276
    | |   |||||||||| | ||| ||||  ||||| |||||||| || ||
4531 GCGTTCAAGTTTTGATCGGTCTCACGGTTATAAGACTACGTTTGATATGG   4580

277 GTTACCTAATCCCTATCTTTTGTGATGAAGTTCTCCCTGGAGATACTTTC    326
    |||  || || ||||  |||| |||||||||||| |||||||||||||||
4581 ATTATTTAGTTCCATTTTTTGTTGATGAAGTTCTTCCTGGAGATACTTTT   4630

327 TCCTTGAAAGAGGCGTTTTTAGCACGTATGGCAACGCCTATCTTTCCTCT    376
    || ||  |||  || ||| ||  || || | | |  || ||| || || |
4631 TCTTTATCGGAGACGCATCTTTGTCGTTTGACTACGTTAGTTCAACCGAT   4680

377 TATGGATAATTTGCGTTTAGATACGCAGTATTTCTTTGTTCCTCTTCGAC    426
    |||||||||| | ||| | ||||| |||| |||||||||||||  |||
4681 TATGGATAATATTCAGTTAACTACTCAGTTTTTCTTTGTTCCCAATCGTT   4730

427 TGTTATGGTCGAATTTCCAAAAGTTCTGTGGAGAACAAGATAATCCTGGA    476
    || | ||| |   ||||  ||||  ||| || | ||  |||||| ||||
4731 TGCTTTGGGATAATTGGGAATCGTTTATTACAGGTGGTGATGAGCCTGTA   4780

477 GATTCCACA..................GATTTTCTTACCCCAGTTTT      505
    | || |||                   |||| || || ||  ||    |
4781 GCTTGGACAAGCACTAATCCTGCTAATGAGTATTTTGTTCCTCAAG...T  4827

506 AACCGCTCCTAGTGGGGGATTTATTGAAGGATCAATCCATGATTATCTTG    555
    ||| ||||| || || ||  | ||||  || |||||||| |||||| |||
4828 AACTTCTCCTGATGGAGGTTACGCAGAGAATTCTATTTATGACTATTTTG   4877

556 GTCTACCTACTAAAGTTGCAGGAATTGAATGTGTTGCGTTCTGGCA..CA    603
    ||||||||||||||||||||    ||  | ||  |||   ||   |  ||
  1 GTCTACCTACTAAAGTTGCA...AATTATCGGCATCAAGTTTTGCCATTAA  48

604 GAGCTTACAATCTGATTTGGAACCAGTACTATCGTGATGAGAATATTCAG    653
    |||| || |||| ||||| ||  | ||||||||||||||||||| |||||
 49 GAGCATATAATTTGATATTTAATGAGTATTATCGTGATGAGAATCTTCAG   98

654 GAATCTGTTGACGTGGAAATGGGAGACACCACCTCTAATG..........   693
    ||| ||  | |||| |||||| |  | ||      |  ||
 99 GAGTCTTTACCTGTTTGGACAGGAGATGCTGATCCTAAGGTTGATCCGAC  148

694 ...AGGTGAACAAT.....................TATAAGC          711
       | ||| |||                        ||||||
149 TACTGGAGAAGAATCTCAAGAGGATGATGCAGTTCCTTATGTATATAAGT  198
```

FIG. 1A

```
                GTTATGATTACTTCACTTCATGTCTCCCTTGG                761
                | |  || |||||||||||||| |||||  ||| ||| |||||
    199 TAATGCGTCGCAATAAGCGATATGATTATTTTACTTCTGCTCTTCCTGGT      248

762 CCACAAAAAGGTCCTGCAG..........TGACAATTGGAGTTGGAGG        799
        || |||||||||| ||              | |||| ||||| | |||
    249 TTGCAGAAAGGTCCTTCTGTTGGAATAGGTATTACAGGTGGAGATTCAGG      298

800 TATTGTTCCTGTTCAAGGTTTAGGAATTCAA.......TGGGGA...ATT      840
        | |||| |||||| |||||  ||| ||||| |||   ||| || |||
    299 ACGTCTTCCAGTTCATGGTTTAGCGATTAGATCTTATTTGGATGATTCTT      348

841 CTAGTGCCCCAAATCCTATAACTGCTTCTAGTTGGATAAATTCCGTTAAT      890
        || ||| | |    | ||    || ||| |           || ||  ||
    349 CTGATGATCAGTTTAGTTTTGGTGTTTC............TTATGTAAAC      386

891 CCTACATTCATAAATTCTACAACGCCGACG...................       920
        ||  ||   ||||||   |||   ||| |
    387 GCTTCA...CAGAAATGGTTTACTGCAGATGGTCGTTTGACTTCTGGAATG     434

921 ........CCTACAGGAACGAATAAGATTTTGAATTATGGTCAGG....       957
            |||  || ||||| |\ ||  | ||| | |  ||  ||| |||
    435 GGTAGTGTTCCTGTTGGTACAACTGGTAATTTTCCTATTGATAATGTTGT      484

958 ........CGTATTATATTAAGA.........AGCCTGGAGAAGCAACAA      990
              | |||| |  |||| ||       | |||| |   ||| |
    485 GTATCCATCTTATTTTGGTACGACTGTTGCCCAAACTGGTAGTCCATCTT      534

991 CAGATCCTACACC....................TAGGGCTTATGTAGAT       1019
        |  | |||| ||                           |  ||||||  |||
    535 CTTCTTCTACTCCGCCTTTTGTTAAGGGTGATTTTCCTGTTTATGTTGAT     584

1020 TTAGGTTCGACTTCTCCTGTGACGATTAATTCTCTTCGTGAAGCTTTCCA     1069
         |||    |    |  ||| || |||||||||| |||||| |  ||    |
    585 TTAGCGGCTTCATCTTCAGTTACGATTAATTCGCTTCGTAATGCGATTAC      634

1070 ATTGCAAAAGCTTTATGAGAGAGATGCTCGTGGTGGAACAAGGTACATTG     1119
         ||||||  ||  |||||  ||||| ||||| ||||  ||    ||| |||
    635 TTTGCAACAGTGGTTTGAGAAGAGTGCTCGTTATGGAAGTAGATATGTTG      684

1120 AGATTATTCGTTCCCATTTCAATGTGCAGTCTCCAGATGCAAGGTTGCAA     1169
         | |  | ||| ||||   |||  |  | |   ||| |   ||  ||||
    685 AATCTGTTCAAGGTCATTTTGGCGTTCATCTTGGTGATTATCGTGCTCAG      734

1170 CGTGCAGAGTATCTTGGAGGTTCTTCAACTCCTGTGAATATTTCTCCGAT     1219
         || || ||| |   |  || || ||| | | | ||| ||   ||| |||
    735 CGACCAATCTATTTAGGTGGATCTAAGTCTTATGTTTCTGTTAATCCTGT     784

1220 TCCACAGACTTCCTCAACAGACTCCACATCTCCTCAAGGAAATCTTGCTG     1269
         ||||| || ||| | || ||| || |||  | ||||||||||||| |||
    785 AGTACAGAATTCATCTACAGATTCAGTTTCTCCTCAAGGAAATCTTTCTG    834
```

*FIG. 1B*

```
1270 CTTATGGTACAGCGATTGGATCGAAGCGAGTCTTCACAAAGTCTTTCACA 1319
     |||||   ||| |||  |||   ||| |||| ||  |||||||
 835 CTTATGCATTATCTACAGATACTAAACATTTGTTTACGAAGTCTTTTGTT  884

1320 GAGCATGGTGTAATTCTTGGATTAGCCTCTGTACGTGCCGATCTCAACTA 1369
     ||||||||| || |  ||||||| |||||||  |   ||  ||| ||||
 885 GAGCATGGTTTTGTTATAGGTCTTCTTTCAGCTACAGCGGATTTAACTTA  934

1370 TCAGCAAGGTTTGGATAGGATGTGGTCACGAAGAACGCGCTGGGACTTTT 1419
     |||||||||||| ||  | |||||||| | ||| | |  ||| ||| ||
 935 TCAGCAAGGTTTAGAGCGTCAGTGGTCAAGATTAGTCGTTATGATTATT   984

1420 ATTGGCCTGCTCTTAGCCATTTAGGTGAGCAAGCTGTGCTCAATAAAGAG 1469
     |||||||| || ||  |||||| || |||||||||| |  ||||||||||
 985 ATTGGCCTACTTTTGCTCATTTGGGAGAGCAGCCTGTTTATAATAAAGAG 1034

1470 ATTTATTGCCAAGGTCCTGCAGTTAAGGATGCTCAGAATGGTAATGTTGT 1519
     ||||||||||||  ||| |  ||  | ||||  |   ||| ||  | ||
1035 ATTTATTGCCAATCAGATACTGTTATGGATCCT...AGTGGTTCTGCGGT 1081

1520 TGTGGATGAGCAAGTCTTTGGATATCAGGAGAGATTTGCGGAGTATCGCT 1569
      |||| ||     ||||  |||| ||  || | ||  |  |||||||| |
1082 TAATGATGTGC...CTTTTGGTTATCAAGAGCGTTATGCTGAGTATCGTT 1128

1570 ATAAGACTTCGAAAATTACTGGGAAGTICCGATCAAATGCTACAGGTTCT 1619
     |||||  ||||||  |||||||  ||   ||| || |||||||||| ||
1129 ATAAGCCTTCGAAGGTTACTGGATTATTTAGATCTAACGCTACAGGTACT 1178

1620 TTAGATGCATGGCATTTAGCTCAGCAGTTTGAGAATCTTCCAACACTTTC 1669
     |||||| |||||||||| ||||| ||||||||||||||||||||||
1179 CTAGATTCTTGGCATTTGTCTCAGAATTTTGCGAATTTACCTACTTTGAA 1228

1670 TCCAGAGTTTATCGAAGAAAATCCTCCTATGGATCGTGTTGTTGTTGCAG 1719
     |     |||||  |    | | || || |||| ||| | | |  | | |
1229 TGAGACTTTTATTCAGAGTAATACGCCGATAGATAGAGCGTTAGCAGTTC 1278

1720 ATACTGAGCCAGATTTTCTCTTAGATGGTTGGTTTTCATTGCGTTGTGCA 1769
     |   ||| |||||||| |||| ||||  || ||   ||| || |||||
1279 CTGATCAGCCTGATTTTATTTGTGACTTTTACTTTAATTATCGTTGTATT 1328

1770 AGACCAATGCCTGTCTATTCTGTTCCAGGCCTCATTGATCATTTCTAA   1817
     || || ||||| ||||||||||||||||| |    | |      |||
1329 AGGCCTATGCCGGTGTATTCTGTTCCAGGTTTAAGAAGGATT...TAA  1373
```

FIG. 1C

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 4529 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:1:

```
GGATCCTTCG AAAAATCAAT TTGCCGCGCA TCCTGAAGAT TACATTCTCT ATGAGATTGG      60

ATCTTACGAT GACTCTACTG GAAACTTCAT TCCCTTAGAT GTGCCTAAAG CCTTAGGAAC     120

AGGCTTGGAT TTTAAGCACA AACAGTAGGG AAGATATGGT TAGGAATCGG CGTTTGCCTT     180

CAGTTATGAG TCATTCTTTC GCGCAAGTGC CATCAGCGCG AATTCAGAGA AGTTCTTTTG     240

ATAGATCTTG TGGTTTAAAG ACTACATTCG ACGCCGGTTA CCTAATCCCT ATCTTTTGTG     300

ATGAAGTTCT CCCTGGAGAT ACTTTCTCCT TGAAAGAGGC GTTTTAGCA  CGTATGGCAA     360

CGCCTATCTT TCCTCTTATG GATAATTTGC GTTAGATAC  GCAGTATTTC TTTGTTCCTC     420

TTCGACTGTT ATGGTCGAAT TTCCAAAAGT TCTGTGGAGA ACAAGATAAT CCTGGAGATT     480

CCACAGATTT TCTTACCCCA GTTTTAACCG CTCCTAGTGG GGGATTTATT GAAGGATCAA     540

TCCATGATTA TCTTGGTCTA CCTACTAAAG TTGCAGGAAT TGAATGTGTT GCGTTCTGGC     600

ACAGAGCTTA CAATCTGATT TGGAACCAGT ACTATCGTGA TGAGAATATT CAGGAATCTG     660

TTGACGTGGA AATGGGAGAC ACCACCTCTA ATGAGGTGAA CAATTATAAG CTTCTTAAGC     720

GTGGGAAGCG TTATGATTAC TTCACTTCAT GTCTCCCTTG GCCACAAAAA GGTCCTGCAG     780

TGACAATTGG AGTTGGAGGT ATTGTTCCTG TTCAAGGTTT AGGAATTCAA TGGGGGAATT     840

CTAGTGCCCC AAATCCTATA ACTGCTTCTA GTTGGATAAA TTCCGTTAAT CCTACATTCA     900

TAAATTCTAC AACGCCGACG CCTACAGGAA CGAATAAGAT TTTGAATTAT GGTCAGGCGT     960

ATTATATTAA GAAGCCTGGA GAAGCAACAA CAGATCCTAC ACCTAGGGCT TATGTAGATT    1020

TAGGTTCGAC TTCTCCTGTG ACGATTAATT CTCTTCGTGA AGCTTTCCAA TTGCAAAAGC    1080

TTTATGAGAG AGATGCTCGT GGTGGAACAA GGTACATTGA GATTATTCGT TCCCATTTCA    1140

ATGTGCAGTC TCCAGATGCA AGGTTGCAAC GTGCAGAGTA TCTTGGAGGT TCTTCAACTC    1200
```

```
CTGTGAATAT TTCTCCGATT CCACAGACTT CCTCAACAGA CTCCACATCT CCTCAAGGAA    1260
ATCTTGCTGC TTATGGTACA GCGATTGGAT CGAAGCGAGT CTTCACAAAG TCTTTCACAG    1320
AGCATGGTGT AATTCTTGGA TTAGCCTCTG TACGTGCCGA TCTCAACTAT CAGCAAGGTT    1380
TGGATAGGAT GTGGTCACGA AGAACGCGCT GGGACTTTTA TTGGCCTGCT CTTAGCCATT    1440
TAGGTGAGCA AGCTGTGCTC AATAAAGAGA TTTATTGCCA AGGTCCTGCA GTTAAGGATG    1500
CTCAGAATGG TAATGTTGTT GTGGATGAGC AAGTCTTTGG ATATCAGGAG AGATTTGCGG    1560
AGTATCGCTA TAAGACTTCG AAAATTACTG GAAGTTCCG ATCAAATGCT ACAGGTTCTT     1620
TAGATGCATG GCATTTAGCT CAGCAGTTTG AGAATCTTCC AACACTTTCT CCAGAGTTTA    1680
TCGAAGAAAA TCCTCCTATG GATCGTGTTG TTGCTGTAGA TACTGAGCCA GATTTTCTCT    1740
TAGATGGTTG GTTTCATTG CGTTGTGCAA GACCAATGCC TGTCTATTCT GTTCCAGGCC     1800
TCATTGATCA TTTCTAATTT CTACTCAGTT TTCCGGTTTG ATAAACAAA CTCACGTTCG     1860
TAGATAAGTG AGTACGGTGA AGACCAAAAC GGAAAGCTGA GGCGTAAAAA TGTGGAGAAT    1920
TTATGAATCC CGAACAACTT ACGAACACTC TCGGTTCAGC AGTTTCTGGA GTTGCTCAAG    1980
GATTATCCTT TCTCCCTGGA ATAGCTTCCG GAGTTTTAGG ATATCTTGGC GCACAGAAAC    2040
AAAATGCGAC TGCGAAGCAA ATTGCTAGAG AGCAAATGGC TTTTCAGGAG CGCATGTCTA    2100
ATACAGCATA CCAACGTGCT ATGGAAGACA TGAAGAAAGC TGGCCTTAAC CCTATGTTAG    2160
CTTTTCTAA AGGCGGTGCT TCTTCTCCTG CAGGAGCGTC ATGGTCTCCG AATAATCCTG     2220
TAGAGAGCGC GATGAATTCT GGACTTGCCG TGCAAAGACT TACTTATGAA CGTAAGAAAA    2280
TGCAGGCAGA GCTTCAGAAT CTTCGTGAGC AGAACCGTTT GATTAGAAAC CAAGCAATAC    2340
GTGAAGGCTA TCTCGCAGAA CGAGATAAAT ATATGCGTGT TGCTGGAGTT CCTGTAGCTA    2400
CTGAGATGTT AGATAGAACT TCAGGTCTTC TCTCATCTTC AGCTAAGGCA TTTAAGAATC    2460
TTTTTTCAAG AAAAGGAAGG TAGATGTTTA AGTCGGCATA TTCCGAAAAA AAATCTGTAA    2520
AGATGAAGTT CACACAGAAA TCTTTGACGC AACAACACAA CAAAGATGAG TGTGATATTA    2580
ACAACATCGT CGCAAAACTC AACGCTACAG GCGTTTTAGA GCACGTAGAG CGACGATCTC    2640
CACGTTATAT GGACTGTATG GACCCTATGG AGTATTCCGA GGCTCTAAAC GTCGTTATTG    2700
AGGCTCAGGA GCAATTTGAC TCTTTACCAG CGAAAGTTCG TGAACGTTTT GGAAATGATC    2760
CAGAAGCGAT GCTCGATTTC TTGAGCCGTG AAGAAAATTA TGAAGAAGCA AAGGCGTTAG    2820
GTTTTGTTTA TGAAGATGGA ACTTCTGGCG CACCTCACAC ATTTTGTGAA GCTGATCCTA    2880
AAGATGATCA AAATGTGGCA AACCAAGAAC CTGGATTAGC CCAAAAATGA GCAAATTTTG    2940
TGCAAAAAAG TGTGCAAAAA ATGCCCAAAA AAAGGGCCAA AAAATGCCCC CAAAATCGGA    3000
GCATTTTACG AGAGAAAAAC CACTAGCGTA ATACAGTCTA CTTGATCTGT ATTACGCTAG    3060
GTCATACCGA TTCAAGGAAA TATTTGAAAA AATAAGCCCT ATTTAGGGCC CAAAATTTAA    3120
GCTTAAAATG AGGTTAAAAA ATGGCACGAA GAAGATACAG ACTTCCGCGA CGTAGAAGTC    3180
GAAGACTTTT TTCAAGAACT GCATTAAGGA TGCATCCAAG AAATAGGCTT CGAAGAATTA    3240
TGCGTGGCGG CATTAGGTTC TAGTTTTGGA CGTTAAGGAA ATCTTTAAGG TTATGCTAAA    3300
TTAGCTGCTA TGTATAATTT GGCTCGTGAC GAATGTCATA TTCGCACCAT TTAAAAGTTG    3360
TACACAGCAG TTGAAGGCTT GGATGTTGAT TTTTAATGTC TTAGCCTTCA TTTTGGGCTT    3420
GTTGTAACTT TTAAATGAGG CATTAATGAC GTGTGĊCTAC CCTTTCGTAT GTTTATAGA    3480
TTCTGATAAT CAACTCTCTT TTCCCAAAGG TGTGAAGTCT TCTAAACCTT GGGATAAAGT    3540
CCTTTAATTA AATGCTTTAG AGCAAGCGCA ACCCGAAGAG TATCGAGTTC GTTGGGTTTT    3600
```

-continued

| | | | | | |
|---|---|---|---|---|---|
| GATGCCTTGG | CGTAAGTGCA | AGTTTTGCAG | AGTGCAGAAT | GCAAAGATTT | GGTCGTATCG | 3660 |
| TTGCATCCAC | GAAGCATCTT | TATATTCTCA | GAATTGCTTT | TTAACCTTGA | CTTATGAGGA | 3720 |
| TCGTCATCTT | CCAGAGAATG | GCTCTCTGGT | AAGAGATCAT | CCGGCTTTGT | TTCTTATGCG | 3780 |
| ATTGAGGAAA | GAGATTTATC | CTCATAAAAT | TCGTTATTTT | GGATGTGGTG | AATATGGATC | 3840 |
| GAAATTACAA | AGGCCTCATT | ATCATCTTCT | TATTTATAAT | TACGATTTTC | CTGATAAGAA | 3900 |
| GCTCTTGAGT | AAAAAGCGTG | GCAATCCTCT | CTTTGTTTCT | GAGAAGTTAA | TGCGGCTTTG | 3960 |
| GCCTTTTGGA | TTCTCTACAG | TAGGATCAGT | AATGCGGCAG | AGTGCAGGTT | ATGTAGCGCG | 4020 |
| GTATTCTTTG | AAGAAGGTGA | ATGGAGATAT | TTCTCAAGAT | CATTACGGAC | AAAGACTTCC | 4080 |
| GCAGTTTCTT | ATGTGTTCTC | TTAAACCAGG | AATAGGAGCC | GATTGGTATG | AGAAATATAA | 4140 |
| ACGCGATGTC | TATCCTCAGG | ATTATCTTGT | TGTGCAAGAT | AAAGGGAAGT | CTTTTACGAC | 4200 |
| GCGTCCTCCA | CGTTACTATG | ATAAGCTACA | TTCTCGGTTT | GATCCGGAAG | AGATGGACGA | 4260 |
| GGTCAAACAA | AAACGTATAG | AGAAAGTTAT | GGCTCTGCCT | CAGTTAACTC | AAGATAAGGC | 4320 |
| TGAGGTGAAG | CAGTATATTT | TCAATGACCG | TACGAAGAGA | CTTTTAGAG | ACTATGAGGA | 4380 |
| GGAGAGTTAC | TAAACTTTTT | TAAAAAATAG | GAGCTTTTT | CAATGAAAGT | TTTTACAGTG | 4440 |
| TTTGATATTA | AGACGGAAAT | TTATCAGCAG | CCTTTTTTA | TGCAGGCTAC | GGGAGCGGCA | 4500 |
| ATCAGAGCGT | TTTCCGATAT | GGTAAATGA | | | | 4529 |

( 2 ) INFORMATION FOR SEQ ID NO:2:

( i ) SEQUENCE CHARACTERISTICS:
( A ) LENGTH: 1662 base pairs
( B ) TYPE: nucleic acid
( C ) STRANDEDNESS: single
( D ) TOPOLOGY: circular ( i i ) MOLECULE TYPE: DNA (genomic)

( x i ) SEQUENCE DESCRIPTION: SEQ ID NO:2:

| | | | | | |
|---|---|---|---|---|---|
| ATGGTTAGGA | ATCGGCGTTT | GCCTTCAGTT | ATGAGTCATT | CTTTCGCGCA | AGTGCCATCA | 60 |
| GCGCGAATTC | AGAGAAGTTC | TTTTGATAGA | TCTTGTGGTT | TAAAGACTAC | ATTCGACGCC | 120 |
| GGTTACCTAA | TCCCTATCTT | TTGTGATGAA | GTTCTCCCTG | GAGATACTTT | CTCCTTGAAA | 180 |
| GAGGCGTTTT | TAGCACGTAT | GGCAACGCCT | ATCTTTCCTC | TTATGGATAA | TTTGCGTTTA | 240 |
| GATACGCAGT | ATTTCTTTGT | TCCTCTTCGA | CTGTTATGGT | CGAATTTCCA | AAAGTTCTGT | 300 |
| GGAGAACAAG | ATAATCCTGG | AGATTCCACA | GATTTTCTTA | CCCCAGTTTT | AACCGCTCCT | 360 |
| AGTGGGGGAT | TTATTGAAGG | ATCAATCCAT | GATTATCTTG | GTCTACCTAC | TAAAGTTGCA | 420 |
| GGAATTGAAT | GTGTTGCGTT | CTGGCACAGA | GCTTACAATC | TGATTTGGAA | CCAGTACTAT | 480 |
| CGTGATGAGA | ATATTCAGGA | ATCTGTTGAC | GTGGAAATGG | GAGACACCAC | CTCTAATGAG | 540 |
| GTGAACAATT | ATAAGCTTCT | TAAGCGTGGG | AAGCGTTATG | ATTACTTCAC | TTCATGTCTC | 600 |
| CCTTGGCCAC | AAAAAGGTCC | TGCAGTGACA | ATTGGAGTTG | GAGGTATTGT | TCCTGTTCAA | 660 |
| GGTTTAGGAA | TTCAATGGGG | GAATTCTAGT | GCCCAAATC | CTATAACTGC | TTCTAGTTGG | 720 |
| ATAAATTCCG | TTAATCCTAC | ATTCATAAAT | TCTACAACGC | CGACGCCTAC | AGGAACGAAT | 780 |
| AAGATTTGA | ATTATGGTCA | GGCGTATTAT | ATTAAGAAGC | CTGGAGAAGC | AACAACAGAT | 840 |
| CCTACACCTA | GGGCTTATGT | AGATTTAGGT | TCGACTTCTC | CTGTGACGAT | TAATTCTCTT | 900 |
| CGTGAAGCTT | CCAATTGCA | AAAGCTTTAT | GAGAGAGATG | CTCGTGGTGG | AACAAGGTAC | 960 |
| ATTGAGATTA | TTCGTTCCCA | TTTCAATGTG | CAGTCTCCAG | ATGCAAGGTT | GCAACGTGCA | 1020 |
| GAGTATCTTG | GAGGTTCTTC | AACTCCTGTG | AATATTTCTC | CGATTCCACA | GACTTCCTCA | 1080 |

| ACAGACTCCA | CATCTCCTCA | AGGAAATCTT | GCTGCTTATG | GTACAGCGAT | TGGATCGAAG | 1140 |
| CGAGTCTTCA | CAAAGTCTTT | CACAGAGCAT | GGTGTAATTC | TTGGATTAGC | CTCTGTACGT | 1200 |
| GCCGATCTCA | ACTATCAGCA | AGGTTTGGAT | AGGATGTGGT | CACGAAGAAC | GCGCTGGGAC | 1260 |
| TTTTATTGGC | CTGCTCTTAG | CCATTTAGGT | GAGCAAGCTG | TGCTCAATAA | AGAGATTTAT | 1320 |
| TGCCAAGGTC | CTGCAGTTAA | GGATGCTCAG | AATGGTAATG | TTGTTGTGGA | TGAGCAAGTC | 1380 |
| TTTGGATATC | AGGAGAGATT | TGCGGAGTAT | CGCTATAAGA | CTTCGAAAAT | TACTGGGAAG | 1440 |
| TTCCGATCAA | ATGCTACAGG | TTCTTTAGAT | GCATGGCATT | TAGCTCAGCA | GTTTGAGAAT | 1500 |
| CTTCCAACAC | TTTCTCCAGA | GTTTATCGAA | GAAAATCCTC | CTATGGATCG | TGTTGTTGCT | 1560 |
| GTAGATACTG | AGCCAGATTT | TCTCTTAGAT | GGTTGGTTTT | CATTGCGTTG | TGCAAGACCA | 1620 |
| ATGCCTGTCT | ATTCTGTTCC | AGGCCTCATT | GATCATTTCT | AA |  | 1662 |

( 2 ) INFORMATION FOR SEQ ID NO:3:

( i ) SEQUENCE CHARACTERISTICS:
        ( A ) LENGTH: 561 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:3:

| ATGAATCCCG | AACAACTTAC | GAACACTCTC | GGTTCAGCAG | TTTCTGGAGT | TGCTCAAGGA | 60 |
| TTATCCTTTC | TCCCTGGAAT | AGCTTCCGGA | GTTTAGGAT | ATCTTGGCGC | ACAGAAACAA | 120 |
| AATGCGACTG | CGAAGCAAAT | TGCTAGAGAG | CAAATGGCTT | TTCAGGAGCG | CATGTCTAAT | 180 |
| ACAGCATACC | AACGTGCTAT | GGAAGACATG | AAGAAAGCTG | GCCTTAACCC | TATGTTAGCT | 240 |
| TTTTCTAAAG | GCGGTGCTTC | TTCTCCTGCA | GGAGCGTCAT | GGTCTCCGAA | TAATCCTGTA | 300 |
| GAGAGCGCGA | TGAATTCTGG | ACTTGCCGTG | CAAAGACTTA | CTTATGAACG | TAAGAAAATG | 360 |
| CAGGCAGAGC | TTCAGAATCT | TCGTGAGCAG | AACCGTTTGA | TTAGAAACCA | AGCAATACGT | 420 |
| GAAGGCTATC | TCGCAGAACG | AGATAAATAT | ATGCGTGTTG | CTGGAGTTCC | TGTAGCTACT | 480 |
| GAGATGTTAG | ATAGAACTTC | AGGTCTTCTC | TCATCTTCAG | CTAAGGCATT | TAAGAATCTT | 540 |
| TTTTCAAGAA | AAGGAAGGTA | G |  |  |  | 561 |

( 2 ) INFORMATION FOR SEQ ID NO:4:

( i ) SEQUENCE CHARACTERISTICS:
        ( A ) LENGTH: 447 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:4:

| ATGTTTAAGT | CGGCATATTC | CGAAAAAAAA | TCTGTAAAGA | TGAAGTTCAC | ACAGAAATCT | 60 |
| TTGACGCAAC | AACACAACAA | AGATGAGTGT | GATATTAACA | ACATCGTCGC | AAAACTCAAC | 120 |
| GCTACAGGCG | TTTTAGAGCA | CGTAGAGCGA | CGATCTCCAC | GTTATATGGA | CTGTATGGAC | 180 |
| CCTATGGAGT | ATTCCGAGGC | TCTAAACGTC | GTTATTGAGG | CTCAGGAGCA | ATTTGACTCT | 240 |
| TTACCAGCGA | AAGTTCGTGA | ACGTTTTGGA | AATGATCCAG | AAGCGATGCT | CGATTTCTTG | 300 |
| AGCCGTGAAG | AAAATTATGA | AGAAGCAAAG | GCGTTAGGTT | TTGTTTATGA | AGATGGAACT | 360 |
| TCTGGCGCAC | CTCACACATT | TTGTGAAGCT | GATCCTAAAG | ATGATCAAAA | TGTGGCAAAC | 420 |

-continued

```
CAAGAACCTG GATTAGCCCA AAAATGA                                                                    447
```

( 2 ) INFORMATION FOR SEQ ID NO:5:

( i ) SEQUENCE CHARACTERISTICS:
        ( A ) LENGTH: 792 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:5:

```
ATGCCTTGGC GTAAGTGCAA GTTTTGCAGA GTGCAGAATG CAAAGATTTG GTCGTATCGT          60
TGCATCCACG AAGCATCTTT ATATTCTCAG AATTGCTTTT TAACCTTGAC TTATGAGGAT         120
CGTCATCTTC CAGAGAATGG CTCTCTGGTA AGAGATCATC CGGCTTTGTT TCTTATGCGA         180
TTGAGGAAAG AGATTTATCC TCATAAAATT CGTTATTTTG GATGTGGTGA ATATGGATCG         240
AAATTACAAA GGCCTCATTA TCATCTTCTT ATTTATAATT ACGATTTTCC TGATAAGAAG         300
CTCTTGAGTA AAAAGCGTGG CAATCCTCTC TTTGTTTCTG AGAAGTTAAT GCGGCTTTGG         360
CCTTTTGGAT TCTCTACAGT AGGATCAGTA ATGCGGCAGA GTGCAGGTTA TGTAGCGCGG         420
TATTCTTTGA AGAAGGTGAA TGGAGATATT TCTCAAGATC ATTACGGACA AAGACTTCCG         480
CAGTTTCTTA TGTGTTCTCT TAAACCAGGA ATAGGAGCCG ATTGGTATGA AAATATAAA          540
CGCGATGTCT ATCCTCAGGA TTATCTTGTT GTGCAAGATA AAGGGAAGTC TTTTACGACG         600
CGTCCTCCAC GTTACTATGA TAAGCTACAT TCTCGGTTTG ATCCGGAAGA GATGGACGAG         660
GTCAAACAAA AACGTATAGA GAAAGTTATG GCTCTGCCTC AGTTAACTCA AGATAAGGCT         720
GAGGTGAAGC AGTATATTTT CAATGACCGT ACGAAGAGAC TTTTAGAGA CTATGAGGAG         780
GAGAGTTACT AA                                                             792
```

( 2 ) INFORMATION FOR SEQ ID NO:6:

( i ) SEQUENCE CHARACTERISTICS:
        ( A ) LENGTH: 553 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:6:

```
Met Val Arg Asn Arg Arg Leu Pro Ser Val Met Ser His Ser Phe Ala
 1               5                  10                  15
Gln Val Pro Ser Ala Arg Ile Gln Arg Ser Ser Phe Asp Arg Ser Cys
                20                  25                  30
Gly Leu Lys Thr Thr Phe Asp Ala Gly Tyr Leu Ile Pro Ile Phe Cys
            35                  40                  45
Asp Glu Val Leu Pro Gly Asp Thr Phe Ser Leu Lys Glu Ala Phe Leu
        50                  55                  60
Ala Arg Met Ala Thr Pro Ile Phe Pro Leu Met Asp Asn Leu Arg Leu
65                  70                  75                  80
Asp Thr Gln Tyr Phe Phe Val Pro Leu Arg Leu Leu Trp Ser Asn Phe
                85                  90                  95
Gln Lys Phe Cys Gly Glu Gln Asp Asn Pro Gly Asp Ser Thr Asp Phe
               100                 105                 110
Leu Thr Pro Val Leu Thr Ala Pro Ser Gly Gly Phe Ile Glu Gly Ser
           115                 120                 125
```

Ile His Asp Tyr Leu Gly Leu Pro Thr Lys Val Ala Gly Ile Glu Cys
130                     135                 140

Val Ala Phe Trp His Arg Ala Tyr Asn Leu Ile Trp Asn Gln Tyr Tyr
145                 150                 155                 160

Arg Asp Glu Asn Ile Gln Glu Ser Val Asp Val Glu Met Gly Asp Thr
                165                 170                 175

Thr Ser Asn Glu Val Asn Asn Tyr Lys Leu Leu Lys Arg Gly Lys Arg
            180                 185                 190

Tyr Asp Tyr Phe Thr Ser Cys Leu Pro Trp Pro Gln Lys Gly Pro Ala
        195                 200                 205

Val Thr Ile Gly Val Gly Gly Ile Val Pro Val Gln Gly Leu Gly Ile
    210                 215                 220

Gln Trp Gly Asn Ser Ser Ala Pro Asn Pro Ile Thr Ala Ser Ser Trp
225                 230                 235                 240

Ile Asn Ser Val Asn Pro Thr Phe Ile Asn Ser Thr Thr Pro Thr Pro
                245                 250                 255

Thr Gly Thr Asn Lys Ile Leu Asn Tyr Gly Gln Ala Tyr Tyr Ile Lys
            260                 265                 270

Lys Pro Gly Glu Ala Thr Thr Asp Pro Thr Pro Arg Ala Tyr Val Asp
        275                 280                 285

Leu Gly Ser Thr Ser Pro Val Thr Ile Asn Ser Leu Arg Glu Ala Phe
    290                 295                 300

Gln Leu Gln Lys Leu Tyr Glu Arg Asp Ala Arg Gly Gly Thr Arg Tyr
305                 310                 315                 320

Ile Glu Ile Ile Arg Ser His Phe Asn Val Gln Ser Pro Asp Ala Arg
                325                 330                 335

Leu Gln Arg Ala Glu Tyr Leu Gly Gly Ser Ser Thr Pro Val Asn Ile
            340                 345                 350

Ser Pro Ile Pro Gln Thr Ser Ser Thr Asp Ser Thr Ser Pro Gln Gly
        355                 360                 365

Asn Leu Ala Ala Tyr Gly Thr Ala Ile Gly Ser Lys Arg Val Phe Thr
370                 375                 380

Lys Ser Phe Thr Glu His Gly Val Ile Leu Gly Leu Ala Ser Val Arg
385                 390                 395                 400

Ala Asp Leu Asn Tyr Gln Gln Gly Leu Asp Arg Met Trp Ser Arg Arg
                405                 410                 415

Thr Arg Trp Asp Phe Tyr Trp Pro Ala Leu Ser His Leu Gly Glu Gln
            420                 425                 430

Ala Val Leu Asn Lys Glu Ile Tyr Cys Gln Gly Pro Ala Val Lys Asp
        435                 440                 445

Ala Gln Asn Gly Asn Val Val Asp Glu Gln Val Phe Gly Tyr Gln
450                 455                 460

Glu Arg Phe Ala Glu Tyr Arg Tyr Lys Thr Ser Lys Ile Thr Gly Lys
465                 470                 475                 480

Phe Arg Ser Asn Ala Thr Gly Ser Leu Asp Ala Trp His Leu Ala Gln
                485                 490                 495

Gln Phe Glu Asn Leu Pro Thr Leu Ser Pro Glu Phe Ile Glu Glu Asn
            500                 505                 510

Pro Pro Met Asp Arg Val Val Ala Val Asp Thr Glu Pro Asp Phe Leu
        515                 520                 525

Leu Asp Gly Trp Phe Ser Leu Arg Cys Ala Arg Pro Met Pro Val Tyr
    530                 535                 540

Ser Val Pro Gly Leu Ile Asp His Phe 545            550

(2) INFORMATION FOR SEQ ID NO:7:

(i) SEQUENCE CHARACTERISTICS:
        (A) LENGTH: 186 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

```
Met Asn Pro Glu Gln Leu Thr Asn Thr Leu Gly Ser Ala Val Ser Gly
1               5                   10                  15

Val Ala Gln Gly Leu Ser Phe Leu Pro Gly Ile Ala Ser Gly Val Leu
            20                  25                  30

Gly Tyr Leu Gly Ala Gln Lys Gln Asn Ala Thr Ala Lys Gln Ile Ala
        35                  40                  45

Arg Glu Gln Met Ala Phe Gln Glu Arg Met Ser Asn Thr Ala Tyr Gln
    50                  55                  60

Arg Ala Met Glu Asp Met Lys Lys Ala Gly Leu Asn Pro Met Leu Ala
65                  70                  75                  80

Phe Ser Lys Gly Gly Ala Ser Ser Pro Ala Gly Ala Ser Trp Ser Pro
            85                  90                  95

Asn Asn Pro Val Glu Ser Ala Met Asn Ser Gly Leu Ala Val Gln Arg
            100                 105                 110

Leu Thr Tyr Glu Arg Lys Lys Met Gln Ala Glu Leu Gln Asn Leu Arg
        115                 120                 125

Glu Gln Asn Arg Leu Ile Arg Asn Gln Ala Ile Arg Glu Gly Tyr Leu
    130                 135                 140

Ala Glu Arg Asp Lys Tyr Met Arg Val Ala Gly Val Pro Val Ala Thr
145                 150                 155                 160

Glu Met Leu Asp Arg Thr Ser Gly Leu Leu Ser Ser Ser Ala Lys Ala
            165                 170                 175

Phe Lys Asn Leu Phe Ser Arg Lys Gly Arg
            180                 185
```

(2) INFORMATION FOR SEQ ID NO:8:

(i) SEQUENCE CHARACTERISTICS:
        (A) LENGTH: 148 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

```
Met Phe Lys Ser Ala Tyr Ser Glu Lys Lys Ser Val Lys Met Lys Phe
1               5                   10                  15

Thr Gln Lys Ser Leu Thr Gln Gln His Asn Lys Asp Glu Cys Asp Ile
            20                  25                  30

Asn Asn Ile Val Ala Lys Leu Asn Ala Thr Gly Val Leu Glu His Val
            35                  40                  45

Glu Arg Arg Ser Pro Arg Tyr Met Asp Cys Met Asp Pro Met Glu Tyr
    50                  55                  60

Ser Glu Ala Leu Asn Val Val Ile Glu Ala Gln Glu Gln Phe Asp Ser
65                  70                  75                  80

Leu Pro Ala Lys Val Arg Glu Arg Phe Gly Asn Asp Pro Glu Ala Met
```

```
                            85                              90                              95
Leu Asp Phe Leu Ser Arg Glu Glu Asn Tyr Glu Glu Ala Lys Ala Leu
                100                             105                     110

Gly Phe Val Tyr Glu Asp Gly Thr Ser Gly Ala Pro His Thr Phe Cys
            115                     120                 125

Glu Ala Asp Pro Lys Asp Asp Gln Asn Val Ala Asn Gln Glu Pro Gly
        130                 135                 140

Leu Ala Gln Lys
145
```

(2) INFORMATION FOR SEQ ID NO:9:

(i) SEQUENCE CHARACTERISTICS:
        (A) LENGTH: 263 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

```
Met Pro Trp Arg Lys Cys Lys Phe Cys Arg Val Gln Asn Ala Lys Ile
1               5                   10                  15

Trp Ser Tyr Arg Cys Ile His Glu Ala Ser Leu Tyr Ser Gln Asn Cys
            20                  25                  30

Phe Leu Thr Leu Thr Tyr Glu Asp Arg His Leu Pro Glu Asn Gly Ser
            35                  40                  45

Leu Val Arg Asp His Pro Ala Leu Phe Leu Met Arg Leu Arg Lys Glu
        50                  55                  60

Ile Tyr Pro His Lys Ile Arg Tyr Phe Gly Cys Gly Glu Tyr Gly Ser
65                  70                  75                  80

Lys Leu Gln Arg Pro His Tyr His Leu Leu Ile Tyr Asn Tyr Asp Phe
                85                  90                  95

Pro Asp Lys Lys Leu Leu Ser Lys Lys Arg Gly Asn Pro Leu Phe Val
            100                 105                 110

Ser Glu Lys Leu Met Arg Leu Trp Pro Phe Gly Phe Ser Thr Val Gly
        115                 120                 125

Ser Val Met Arg Gln Ser Ala Gly Tyr Val Ala Arg Tyr Ser Leu Lys
        130                 135                 140

Lys Val Asn Gly Asp Ile Ser Gln Asp His Tyr Gly Gln Arg Leu Pro
145                 150                 155                 160

Gln Phe Leu Met Cys Ser Leu Lys Pro Gly Ile Gly Ala Asp Trp Tyr
                165                 170                 175

Glu Lys Tyr Lys Arg Asp Val Tyr Pro Gln Asp Tyr Leu Val Val Gln
            180                 185                 190

Asp Lys Gly Lys Ser Phe Thr Thr Arg Pro Pro Arg Tyr Tyr Asp Lys
        195                 200                 205

Leu His Ser Arg Phe Asp Pro Glu Glu Met Asp Glu Val Lys Gln Lys
    210                 215                 220

Arg Ile Glu Lys Val Met Ala Leu Pro Gln Leu Thr Gln Asp Lys Ala
225                 230                 235                 240

Glu Val Lys Gln Tyr Ile Phe Asn Asp Arg Thr Lys Arg Leu Phe Arg
                245                 250                 255

Asp Tyr Glu Glu Glu Ser Tyr
            260
```

(2) INFORMATION FOR SEQ ID NO:10:

( i ) SEQUENCE CHARACTERISTICS:
    ( A ) LENGTH: 1791 base pairs
    ( B ) TYPE: nucleic acid
    ( C ) STRANDEDNESS: single
    ( D ) TOPOLOGY: circular ( i i ) MOLECULE TYPE: DNA (genomic)

( x i ) SEQUENCE DESCRIPTION: SEQ ID NO:10:

```
ATGGCTAAAG GACGAAAGCT TCCGTCGGTT ATGAAGAATC GTTTTTCAGA GGTACCGACA        60
GCTACGATTA GGCGTTCAAG TTTTGATCGG TCTCACGGTT ATAAGACTAC GTTTGATATG       120
GATTATTTAG TTCCATTTTT TGTTGATGAA GTTCTTCCTG GAGATACTTT TTCTTTATCG       180
GAGACGCATC TTTGTCGTTT GACTACGTTA GTTCAACCGA TTATGGATAA TATTCAGTTA       240
ACTACTCAGT TTTTCTTTGT TCCCAATCGT TTGCTTTGGG ATAATTGGGA ATCGTTTATT       300
ACAGGTGGTG ATGAGCCTGT AGCTTGGACA AGCACTAATC CTGCTAATGA GTATTTTGTT       360
CCTCAAGTAA CTTCTCCTGA TGGAGGTTAC GCAGAGAATT CTATTTATGA CTATTTTGGT       420
CTACCTACTA AAGTTGCAAA TTATCGGCAT CAAGTTTTGC CATTAAGAGC ATATAATTTG       480
ATATTTAATG AGTATTATCG TGATGAGAAT CTTCAGGAGT CTTTACCTGT TTGGACAGGA       540
GATGCTGATC CTAAGGTTGA TCCGACTACT GGAGAAGAAT CTCAAGAGGA TGATGCAGTT       600
CCTTATGTAT ATAAGTTAAT GCGTCGCAAT AAGCGATATG ATTATTTTAC TTCTGCTCTT       660
CCTGGTTTGC AGAAAGGTCC TTCTGTTGGA ATAGGTATTA CAGGTGGAGA TTCAGGACGT       720
CTTCCAGTTC ATGGTTTAGC GATTAGATCT TATTTGGATG ATTCTTCTGA TGATCAGTTT       780
AGTTTTGGTG TTTCTTATGT AAACGCTTCA CAGAAATGGT TTACTGCAGA TGGTCGTTTG       840
ACTTCTGGAA TGGGTAGTGT TCCTGTTGGT ACAACTGGTA ATTTTCCTAT TGATAATGTT       900
GTGTATCCAT CTTATTTTGG TACGACTGTT GCCCAAACTG GTAGTCCATC TTCTTCTTCT       960
ACTCCGCCTT TTGTTAAGGG TGATTTTCCT GTTTATGTTG ATTAGCGGC TTCATCTTCA       1020
GTTACGATTA ATTCGCTTCG TAATGCGATT ACTTTGCAAC AGTGGTTTGA GAAGAGTGCT      1080
CGTTATGGAA GTAGATATGT TGAATCTGTT CAAGGTCATT TTGGCGTTCA TCTTGGTGAT      1140
TATCGTGCTC AGCGACCAAT CTATTTAGGT GGATCTAAGT CTTATGTTTC TGTTAATCCT      1200
GTAGTACAGA ATTCATCTAC AGATTCAGTT TCTCCTCAAG GAAATCTTTC TGCTTATGCA      1260
TTATCTACAG ATACTAAACA TTTGTTTACG AAGTCTTTTG TTGAGCATGG TTTTGTTATA      13·20
GGTCTTCTTT CAGCTACAGC GGATTTAACT TATCAGCAAG GTTAGAGCG TCAGTGGTCA       1380
AGATTTAGTC GTTATGATTA TTATTGGCCT ACTTTTGCTC ATTTGGGAGA GCAGCCTGTT      1440
TATAATAAAG AGATTTATTG CCAATCAGAT ACTGTTATGG ATCCTAGTGG TTCTGCGGTT      1500
AATGATGTGC CTTTTGGTTA TCAAGAGCGT TATGCTGAGT ATCGTTATAA GCCTTCGAAG      1560
GTTACTGGAT TATTTAGATC TAACGCTACA GGTACTCTAG ATTCTTGGCA TTTGTCTCAG      1620
AATTTTGCGA ATTACCTAC TTTGAATGAG ACTTTTATTC AGAGTAATAC GCCGATAGAT       1680
AGAGCGTTAG CAGTTCCTGA TCAGCCTGAT TTATTTGTG ACTTTTACTT TAATTATCGT       1740
TGTATTAGGC CTATGCCGGT GTATTCTGTT CCAGGTTTAA GAAGGATTTA A              1791
```

( 2 ) INFORMATION FOR SEQ ID NO:11:

( i ) SEQUENCE CHARACTERISTICS:
        ( A ) LENGTH: 596 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:11:

| Met | Ala | Lys | Gly | Arg | Lys | Leu | Pro | Ser | Val | Met | Lys | Asn | Arg | Phe | Ser |
|---|---|---|---|---|---|---|---|---|---|---|---|---|---|---|---|
| 1 | | | | 5 | | | | | 10 | | | | | 15 | |
| Glu | Val | Pro | Thr | Ala | Thr | Ile | Arg | Arg | Ser | Ser | Phe | Asp | Arg | Ser | His |
| | | | 20 | | | | | 25 | | | | | 30 | | |
| Gly | Tyr | Lys | Thr | Thr | Phe | Asp | Met | Asp | Tyr | Leu | Val | Pro | Phe | Phe | Val |
| | | 35 | | | | | 40 | | | | | 45 | | | |
| Asp | Glu | Val | Leu | Pro | Gly | Asp | Thr | Phe | Ser | Leu | Ser | Glu | Thr | His | Leu |
| | 50 | | | | 55 | | | | | | 60 | | | | |
| Cys | Arg | Leu | Thr | Thr | Leu | Val | Gln | Pro | Leu | Met | Asp | Asn | Ile | Gln | Leu |
| 65 | | | | 70 | | | | | 75 | | | | | 80 | |
| Thr | Thr | Gln | Phe | Phe | Phe | Val | Pro | Asn | Arg | Leu | Leu | Trp | Asp | Asn | Trp |
| | | | | 85 | | | | | 90 | | | | | 95 | |
| Glu | Ser | Phe | Ile | Thr | Gly | Gly | Asp | Glu | Pro | Val | Ala | Trp | Thr | Ser | Thr |
| | | | 100 | | | | | 105 | | | | | 110 | | |
| Asn | Pro | Ala | Asn | Glu | Tyr | Phe | Val | Pro | Gln | Val | Thr | Ser | Pro | Asp | Gly |
| | | | 115 | | | | | 120 | | | | | 125 | | |
| Gly | Tyr | Ala | Glu | Asn | Ser | Ile | Tyr | Asp | Tyr | Phe | Gly | Leu | Pro | Thr | Lys |
| | | 130 | | | | | 135 | | | | | 140 | | | |
| Val | Ala | Asn | Tyr | Arg | His | Gln | Val | Leu | Pro | Leu | Arg | Ala | Tyr | Asn | Leu |
| 145 | | | | | 150 | | | | | 155 | | | | | 160 |
| Ile | Phe | Asn | Glu | Tyr | Tyr | Arg | Asp | Glu | Asn | Ile | Gln | Glu | Ser | Leu | Pro |
| | | | | 165 | | | | | 170 | | | | | 175 | |
| Val | Trp | Thr | Gly | Asp | Ala | Asp | Pro | Lys | Val | Asp | Pro | Thr | Thr | Gly | Glu |
| | | | 180 | | | | | 185 | | | | | 190 | | |
| Glu | Ser | Gln | Glu | Asp | Asp | Ala | Val | Pro | Tyr | Val | Tyr | Lys | Leu | Met | Arg |
| | | | 195 | | | | | 200 | | | | | 205 | | |
| Arg | Asn | Lys | Arg | Tyr | Asp | Tyr | Phe | Thr | Ser | Ala | Leu | Pro | Gly | Leu | Gln |
| | | | 210 | | | | | 215 | | | | | 220 | | |
| Lys | Gly | Pro | Ser | Val | Gly | Ile | Gly | Ile | Thr | Gly | Gly | Asp | Ser | Gly | Arg |
| 225 | | | | | 230 | | | | | 235 | | | | | 240 |
| Leu | Pro | Val | His | Gly | Leu | Ala | Ile | Arg | Ser | Tyr | Leu | Asp | Asp | Ser | Ser |
| | | | | 245 | | | | | 250 | | | | | 255 | |
| Asp | Asp | Gln | Phe | Ser | Phe | Gly | Val | Ser | Tyr | Val | Asn | Ala | Ser | Gln | Lys |
| | | | 260 | | | | | 265 | | | | | 270 | | |
| Trp | Phe | Thr | Ala | Asp | Gly | Arg | Leu | Thr | Ser | Gly | Met | Gly | Ser | Val | Pro |
| | | 275 | | | | | 280 | | | | | 285 | | | |
| Val | Gly | Thr | Thr | Gly | Asn | Phe | Pro | Ile | Asp | Asn | Val | Val | Tyr | Pro | Ser |
| | 290 | | | | | 295 | | | | | 300 | | | | |
| Tyr | Phe | Gly | Thr | Thr | Val | Ala | Gln | Thr | Gly | Ser | Pro | Ser | Ser | Ser | Ser |
| 305 | | | | | 310 | | | | | 315 | | | | | 320 |
| Thr | Pro | Pro | Phe | Val | Lys | Gly | Asp | Phe | Pro | Val | Tyr | Val | Asp | Leu | Ala |
| | | | | 325 | | | | | 330 | | | | | 335 | |
| Ala | Ser | Ser | Ser | Val | Thr | Ile | Asn | Ser | Leu | Arg | Asn | Ala | Ile | Thr | Leu |
| | | | 340 | | | | | 345 | | | | | 350 | | |
| Gln | Gln | Trp | Phe | Glu | Lys | Ser | Ala | Arg | Tyr | Gly | Ser | Arg | Tyr | Val | Glu |
| | | 355 | | | | | 360 | | | | | 365 | | | |
| Ser | Val | Gln | Gly | His | Phe | Gly | Val | His | Leu | Gly | Asp | Tyr | Arg | Ala | Gln |
| | 370 | | | | | 375 | | | | | 380 | | | | |
| Arg | Pro | Ile | Tyr | Leu | Gly | Gly | Ser | Lys | Ser | Tyr | Val | Ser | Val | Asn | Pro |
| 385 | | | | | 390 | | | | | 395 | | | | | 400 |
| Val | Val | Gln | Asn | Ser | Ser | Thr | Asp | Ser | Val | Ser | Pro | Gln | Gly | Asn | Leu |

|       |       |       | 405   |       |       |       | 410   |       |       |       | 415   |       |
|-------|-------|-------|-------|-------|-------|-------|-------|-------|-------|-------|-------|-------|

Ser Ala Tyr Ala Leu Ser Thr Asp Thr Lys His Leu Phe Thr Lys Ser
            420                 425             430

Phe Val Glu His Gly Phe Val Ile Gly Leu Leu Ser Ala Thr Ala Asp
            435                 440             445

Leu Thr Tyr Gln Gln Gly Leu Glu Arg Gln Trp Ser Arg Phe Ser Arg
450                     455                 460

Tyr Asp Tyr Tyr Trp Pro Thr Phe Ala His Leu Gly Glu Gln Pro Val
465                 470             475                     480

Tyr Asn Lys Glu Ile Tyr Cys Gln Ser Asp Thr Val Met Asp Pro Ser
                485             490                     495

Gly Ser Ala Val Asn Asp Val Pro Phe Gly Tyr Gln Glu Arg Tyr Ala
            500                 505                 510

Glu Tyr Arg Tyr Lys Pro Ser Lys Val Thr Gly Leu Phe Arg Ser Asn
            515             520                 525

Ala Thr Gly Thr Leu Asp Ser Trp His Leu Ser Gln Asn Phe Ala Asn
    530                 535                 540

Leu Pro Thr Leu Asn Glu Thr Phe Ile Gln Ser Asn Thr Pro Ile Asp
545                 550                 555                 560

Arg Ala Leu Ala Val Pro Asp Gln Pro Asp Phe Ile Cys Asp Phe Tyr
                565                 570                 575

Phe Asn Tyr Arg Cys Ile Arg Pro Met Pro Val Tyr Ser Val Pro Gly
            580                 585                 590

Leu Arg Arg Ile
            595

( 2 ) INFORMATION FOR SEQ ID NO:12:

( i ) SEQUENCE CHARACTERISTICS:
       ( A ) LENGTH: 553 amino acids
       ( B ) TYPE: amino acid
       ( C ) STRANDEDNESS: Not Relevant
       ( D ) TOPOLOGY: linear ( i i ) MOLECULE TYPE: peptide ( x i ) SEQUENCE DESCRIPTION: SEQ ID NO:12:

Met Lys Lys Lys Met Ser Lys Leu Asn Ala Arg Val His Asp Phe Ser
1               5                   10                  15

Met Phe Lys Gly Asn His Ile Pro Arg Ser Lys Ile His Ile Pro His
            20                  25                  30

Lys Thr Ile Arg Ala Phe Asn Val Gly Glu Ile Ile Pro Ile Tyr Gln
            35                  40                  45

Thr Pro Val Tyr Pro Gly Glu His Ile Lys Met Asp Leu Thr Ser Leu
    50                  55                  60

Tyr Arg Pro Ser Thr Phe Ile Val Pro Pro Met Asp Asp Leu Ile Val
65                  70                  75                  80

Asp Thr Tyr Ala Phe Ala Val Pro Trp Arg Ile Val Trp Lys Asp Leu
                85                  90                  95

Glu Lys Phe Phe Gly Glu Asn Ser Asp Ser Trp Asp Val Lys Asn Ala
            100                 105                 110

Pro Pro Val Pro Asp Ile Val Ala Pro Ser Gly Gly Trp Asp Tyr Gly
            115                 120                 125

Thr Leu Ala Asp His Phe Gly Ile Thr Pro Lys Val Pro Gly Ile Arg
    130                 135                 140

Val Lys Ser Leu Arg Phe Arg Ala Tyr Ala Lys Ile Ile Asn Asp Trp
145                 150                 155                 160

-continued

```
Phe Arg Asp Gln Asn Leu Ser Ser Glu Cys Ala Leu Thr Leu Asp Ser
            165                 170                 175
Ser Asn Ser Gln Gly Ser Asn Gly Ser Asn Gln Val Thr Asp Ile Gln
            180                 185                 190
Leu Gly Gly Lys Pro Tyr Ile Ala Asn Lys Tyr His Asp Tyr Phe Thr
            195                 200                 205
Ser Cys Leu Pro Ala Pro Gln Lys Gly Ala Pro Thr Thr Ile Asn Val
    210                 215                 220
Gly Gly Met Ala Pro Val Thr Thr Lys Phe Arg Asp Val Pro Asn Leu
225                 230                 235                 240
Ser Gly Thr Pro Leu Ile Phe Arg Asp Asn Lys Gly Arg Thr Ile Lys
                245                 250                 255
Thr Gly Gln Leu Gly Ile Gly Pro Val Asp Ala Gly Phe Leu Val Ala
            260                 265                 270
Gln Asn Thr Ala Gln Ala Ala Asn Gly Glu Arg Ala Ile Pro Ser Asn
            275                 280                 285
Leu Trp Ala Asp Leu Ser Asn Ala Thr Gly Ile Ser Ile Ser Asp Leu
    290                 295                 300
Arg Leu Ala Ile Thr Tyr Gln His Tyr Lys Glu Met Asp Ala Arg Gly
305                 310                 315                 320
Gly Thr Arg Tyr Val Glu Phe Thr Leu Asn His Phe Gly Val His Thr
                325                 330                 335
Ala Asp Ala Arg Leu Gln Arg Ser Glu Phe Leu Gly Gly His Ser Gln
            340                 345                 350
Ser Leu Leu Val Gln Ser Val Pro Gln Thr Ser Ser Thr Val Glu Lys
        355                 360                 365
Met Thr Pro Gln Gly Asn Leu Ala Ala Phe Ser Glu Thr Met Ile Gln
    370                 375                 380
Asn Asn Tyr Leu Val Asn Lys Thr Phe Thr Glu His Ser Tyr Ile Ile
385                 390                 395                 400
Val Leu Ala Val Val Arg Tyr Lys His Thr Tyr Gln Gln Gly Ile Glu
                405                 410                 415
Ala Asp Trp Phe Arg Gly Gln Asp Lys Phe Asp Met Tyr Asp Pro Leu
            420                 425                 430
Leu Ala Asn Ile Ser Glu Gln Pro Val Lys Asn Arg Glu Ile Met Val
        435                 440                 445
Gln Gly Asn Ser Gln Asp Asn Glu Ile Phe Gly Phe Gln Glu Ala Trp
    450                 455                 460
Ala Asp Leu Arg Phe Lys Pro Asn Ser Val Ala Gly Val Met Arg Ser
465                 470                 475                 480
Ser His Pro Gln Ser Leu Asp Tyr Trp His Phe Ala Asp His Tyr Ala
                485                 490                 495
Gln Leu Pro Lys Leu Ser Ser Glu Trp Leu Lys Glu Asp Tyr Lys Asn
            500                 505                 510
Val Asp Arg Thr Leu Ala Leu Lys Ala Ser Asp Asn Thr Pro Gln Leu
        515                 520                 525
Arg Val Asp Phe Met Phe Asn Thr Ile Ala Glu Lys Pro Met Pro Leu
    530                 535                 540
Tyr Ser Thr Pro Gly Leu Arg Arg Ile
545                 550
```

( 2 ) INFORMATION FOR SEQ ID NO:13:

( i ) SEQUENCE CHARACTERISTICS:

(A) LENGTH: 263 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:13:

```
Met Ser Phe Ala Glu Asn Val Gly Arg Phe Ile Gly Asn Ser Val Asn
1               5                   10                  15
Ser Val Gly Ser Val Ile Gly Asp Gly Leu Lys Gly Phe Asn Ser Thr
                20                  25                  30
Gln Ser Ile Ser Ser Ala Lys Gln Ala Asn Leu Leu Asn Asn Leu Pro
            35                  40                  45
Leu Pro Ser Leu Asp Asn Val Leu Asn Ile Gly Met Phe Gly Gly Leu
        50                  55                  60
Ala Ser Gly Leu Leu Ser Tyr Arg Ala Ala Lys Gln Asn Lys Val
65                  70                  75                  80
Met Gln Asp Ile Ala Asn Arg Gln Met Ala Phe Gln Glu Arg Met Ser
                85                  90                  95
Ser Thr Ala Val Arg Arg His Val Glu Asp Leu Lys Lys Ala Gly Leu
                100                 105                 110
Asn Pro Leu Leu Ala Leu Gly Gly Ser Ala Ser Thr Pro Gln Gly Ala
            115                 120                 125
Phe Tyr Ser Pro Val Asn Pro Met Glu Ser Gly Leu Asn Ser Ala Ile
    130                 135                 140
Ser Val Ala Asp Lys Val Phe Asp Tyr Gln Arg Leu Ala His Ala Asp
145                 150                 155                 160
Phe Gln Gly Arg Leu Asn Ser Ala Met Ser Val Val Gln Leu Ala Ser
                165                 170                 175
Ala Val Gln Asp Tyr Lys Arg Asn Tyr Gly Lys Phe Gly Glu Val Ala
            180                 185                 190
Tyr Trp Phe Asp Arg Tyr Ala Gly Lys Leu Leu Pro Ala Met Leu Phe
        195                 200                 205
Tyr Leu Phe Arg Lys His Pro Val Gly Arg Ala Val Ser Ala Ala Asn
    210                 215                 220
Ser Gly Tyr Ala Val Ala Lys Gly Ala Lys Gly Val Asn Phe Lys Phe
225                 230                 235                 240
Ser Asn Met Ser Ser Thr Ala Val Gln Arg His Asn Ser Arg Tyr Asn
                245                 250                 255
Val Ser Lys Gly Trp Arg Arg
            260
```

(2) INFORMATION FOR SEQ ID NO:14:

(i) SEQUENCE CHARACTERISTICS:
(A) LENGTH: 133 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:14:

```
Met Gly Pro Leu Leu Gly Met Val Gly Ala Gly Ala Ala Gly Ser Ala
1               5                   10                  15
Ile Gly Glu Gly Leu Gly Met Leu Arg Asp Lys Trp Asn Arg Asp Phe
                20                  25                  30
Gln Glu Arg Met Ser Asn Thr Gln Tyr Gln Arg Ala Arg Lys Asp Met
```

-continued

| | | 35 | | | | 40 | | | | 45 | | | |
|---|---|---|---|---|---|---|---|---|---|---|---|---|---|
| Glu | Ala | Ala | Gly | Ile | Asn | Pro | Leu | Ala | Gln | Phe | Gly | Ser | Gly | Gln | Ala |
| | 50 | | | | | 55 | | | | 60 | | | |
| Ser | Ser | Pro | Ser | Gly | Gly | Val | Ser | Gly | Ser | Ser | Phe | Gly | Ser | Asn | Ile |
| 65 | | | | | 70 | | | | 75 | | | | 80 |
| Thr | Ser | Met | Leu | Gly | Ser | Ser | Ala | Asn | Met | Leu | Met | Gln | Leu | Ser | Lys |
| | | | | 85 | | | | | 90 | | | | | 95 | |
| Leu | Lys | Glu | Asp | Ala | Glu | Arg | Ala | Asn | Phe | Gly | Ser | Lys | Thr | Val | Gln |
| | | | 100 | | | | | 105 | | | | 110 | | |
| Thr | Ile | Asn | Asp | Ala | Arg | Asn | Asn | Met | Val | Arg | Ser | Val | Ile | Thr | Leu |
| | | 115 | | | | | 120 | | | | | 125 | | |
| Ser | Lys | Arg | Val | Lys |
| | 130 | | | |

( 2 ) INFORMATION FOR SEQ ID NO:15:

( i ) SEQUENCE CHARACTERISTICS:
( A ) LENGTH: 145 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:15:

| Met | Lys | Phe | Arg | Thr | Ile | Tyr | Asp | Glu | Glu | Arg | Pro | Ala | Pro | Val | Leu |
|---|---|---|---|---|---|---|---|---|---|---|---|---|---|---|---|
| 1 | | | | 5 | | | | | 10 | | | | | 15 | |
| Glu | Cys | Lys | Asp | Glu | Ser | Leu | Cys | Leu | Ala | Tyr | Gln | Cys | Thr | Glu | Thr |
| | | | 20 | | | | | 25 | | | | 30 | | |
| Ser | Ile | Glu | Lys | Leu | Val | Lys | Leu | Ala | Asn | Gln | Asn | Pro | Ser | Tyr | Leu |
| | | | 35 | | | | | 40 | | | | 45 | | |
| His | Ala | Phe | Ala | Gly | Asp | Pro | Thr | Arg | Gln | Pro | Glu | Tyr | Gly | Glu | Cys |
| | 50 | | | | | 55 | | | | | 60 | | |
| Pro | Ser | Pro | Leu | Asp | Tyr | Gln | Asp | Ala | Leu | Glu | Ile | Val | Ala | Arg | Gly |
| 65 | | | | | 70 | | | | 75 | | | | | 80 |
| Glu | Glu | Ala | Phe | Tyr | Ser | Leu | Pro | Ala | Asn | Ile | Arg | Val | Asn | Phe | Ser |
| | | | | 85 | | | | | 90 | | | | | 95 | |
| Asn | Pro | Met | Glu | Phe | Leu | Ser | Trp | Leu | Glu | Asp | Pro | Ala | Asn | Tyr | Asp |
| | | | 100 | | | | | 105 | | | | 110 | | |
| Glu | Val | Glu | Lys | Leu | Gly | Leu | Leu | Asp | Pro | Glu | Lys | Val | Gln | Ile | Arg |
| | | | 115 | | | | | 120 | | | | 125 | | |
| Lys | Ser | Lys | Leu | Gln | Lys | Asp | Gln | Lys | Glu | Glu | Val | Ser | Ser | Glu | Glu |
| | 130 | | | | | 135 | | | | | 140 | | |
| Lys |
| 145 |

( 2 ) INFORMATION FOR SEQ ID NO:16:

( i ) SEQUENCE CHARACTERISTICS:
( A ) LENGTH: 399 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:16:

| Met | Arg | Tyr | Ser | Leu | Asp | Ser | Tyr | Leu | Ile | Ser | Val | Tyr | Ile | Arg | Leu |
|---|---|---|---|---|---|---|---|---|---|---|---|---|---|---|---|
| 1 | | | | 5 | | | | | 10 | | | | | 15 | |

```
Thr  Gln  Arg  Lys  Ser  Asp  Tyr  Met  Cys  Thr  Asn  Pro  Ile  Ile  Pro  Ile
          20                  25                      30

Val  Gln  Tyr  Lys  Val  Pro  Val  Lys  Ser  Ser  Leu  Asp  Val  Val  Asp  Trp
          35                  40                      45

Ser  Lys  Phe  Arg  Ser  Asn  Phe  Lys  Ala  Asn  Leu  Phe  Phe  Phe  Glu  Lys
     50                       55                      60

Asn  Val  Val  Arg  Arg  Ala  Val  Ser  Asn  Val  Asp  Glu  Ala  Phe  Arg  Phe
65                       70                  75                           80

Thr  Glu  Gln  Leu  Lys  Gln  Val  Ser  Tyr  Leu  Ser  Thr  Phe  Asp  Leu  Asp
               85                       90                       95

Gly  Tyr  His  Gln  Val  Lys  Gln  Phe  Ser  Phe  Pro  Leu  Pro  Cys  Arg  Lys
               100                      105                      110

Cys  Ser  Glu  Cys  Leu  Gln  Lys  Arg  Ser  Lys  Asp  Leu  Ala  Val  Gln  Ala
          115                      120                      125

Thr  Met  Glu  Ala  Arg  Ser  His  Glu  Glu  Asn  Ser  Val  Leu  Ile  Leu  Thr
     130                      135                      140

Tyr  Asp  Asn  Asp  His  Leu  Gly  Asp  Asn  Ile  Leu  Asp  Tyr  Asp  His  Ile
145                           150                      155                      160

Arg  Val  Phe  Gln  Lys  Arg  Leu  Arg  Arg  Tyr  Val  Asp  Tyr  His  Tyr  Gly
               165                      170                      175

Lys  Lys  Ile  Lys  Phe  Leu  Thr  Val  Gly  Glu  Tyr  Gly  Asp  Lys  Lys  Gly
               180                      185                      190

Arg  Met  His  Trp  His  Met  Ile  Val  Phe  Gly  Trp  Lys  Pro  Lys  Ser  Glu
          195                      200                      205

Glu  Gln  Leu  Glu  Pro  Tyr  Leu  Gly  Gly  Lys  Tyr  Arg  Thr  Asp  Val  Arg
     210                      215                      220

Tyr  Arg  Ser  Arg  Lys  Leu  Lys  Glu  Leu  Trp  Lys  Phe  Gly  Tyr  Val  Asp
225                      230                      235                           240

Val  Asp  Glu  Ala  Thr  Asp  Gly  Asn  Ile  Phe  Tyr  Val  Ala  Arg  Tyr  Val
               245                      250                      255

Gln  Lys  Lys  Phe  Val  Val  Gly  Cys  Asp  Leu  Asp  Ser  Ser  Lys  Ser  Ser
               260                      265                      270

Ser  Arg  Arg  Glu  Lys  Lys  Thr  Ala  Ser  Gln  Ala  Leu  Gly  Leu  Asp  Tyr
          275                      280                      285

Phe  Glu  Ser  Tyr  Leu  Arg  Gln  Phe  Leu  Lys  Thr  Lys  Arg  Ile  Val  Leu
     290                      295                      300

Asn  Gly  Phe  Arg  Tyr  Gly  Phe  Pro  Arg  Tyr  Phe  Lys  Asp  Leu  Leu  Arg
305                      310                      315                           320

Lys  Leu  Val  Ser  Glu  Asp  Ser  Glu  Phe  Asp  Thr  Glu  Tyr  Tyr  Asn  Ala
               325                      330                      335

Leu  Arg  Lys  Arg  Leu  Leu  Ser  Val  Cys  Ser  Tyr  Ser  Met  Val  Asn  Lys
               340                      345                      350

Tyr  Phe  Thr  Tyr  Leu  Glu  Cys  Leu  Val  Glu  Val  Leu  Pro  Val  Leu  Asn
          355                      360                      365

Phe  His  Asp  Leu  Tyr  Gln  Arg  Ala  Leu  Arg  Tyr  Met  Asp  Gln  Ser  Ile
     370                      375                      380

Leu  Lys  Pro  His  Ala  Ser  Asp  His  Asp  Gly  Glu  Tyr  Asn  Thr  Thr
385                      390                      395
```

( 2 ) INFORMATION FOR SEQ ID NO:17:

( i ) SEQUENCE CHARACTERISTICS:
        ( A ) LENGTH: 320 amino acids
        ( B ) TYPE: amino acid
        ( C ) STRANDEDNESS: Not Relevant
        ( D ) TOPOLOGY: linear (ii) MOLECULE TYPE: peptide (xi) SEQUENCE DESCRIPTION: SEQ ID NO:17:

| Met | Ala | Cys | Leu | Arg | Pro | Leu | Gln | Val | His | Asn | Leu | Lys | Lys | Gly | Glu |
|---|---|---|---|---|---|---|---|---|---|---|---|---|---|---|---|
| 1 | | | | 5 | | | | | 10 | | | | | 15 | |
| Lys | Val | Asn | Phe | Lys | His | Tyr | Ser | Asn | Gly | Asp | Val | Ala | Arg | Tyr | Asp |
| | | | 20 | | | | | 25 | | | | | 30 | | |
| Met | Asn | Lys | Asn | Tyr | Ile | Val | Asn | Asp | Ser | Val | Pro | Cys | Arg | Lys | Cys |
| | | 35 | | | | | 40 | | | | | 45 | | | |
| Val | Gly | Cys | Arg | Leu | Asp | Asn | Ser | Ala | Glu | Trp | Gly | Val | Arg | Ala | Ser |
| | 50 | | | | | 55 | | | | | 60 | | | | |
| Leu | Glu | Ile | Lys | Ser | Asn | Pro | Lys | His | Asn | Trp | Phe | Val | Thr | Leu | Thr |
| 65 | | | | | 70 | | | | | 75 | | | | | 80 |
| Tyr | Ser | Asp | Glu | His | Leu | Val | Tyr | Asn | Ala | Leu | Gly | Arg | Pro | Asn | Cys |
| | | | | 85 | | | | | 90 | | | | | 95 | |
| Val | Pro | Glu | His | Ile | Thr | Lys | Phe | Ile | Lys | Ser | Leu | Arg | Lys | Tyr | Phe |
| | | | 100 | | | | | 105 | | | | | 110 | | |
| Glu | Arg | Arg | Gly | His | Ile | Gly | Ile | Lys | Tyr | Leu | Ala | Ser | Asn | Glu | Tyr |
| | | 115 | | | | | 120 | | | | | 125 | | | |
| Gly | Thr | Lys | Arg | Met | Arg | Pro | His | Tyr | His | Ile | Cys | Phe | Phe | Asn | Leu |
| | 130 | | | | | 135 | | | | | 140 | | | | |
| Pro | Leu | Asp | Asp | Leu | Glu | Lys | Thr | Ile | Asp | Ser | Gln | Lys | Gly | Tyr | Gln |
| 145 | | | | | 150 | | | | | 155 | | | | | 160 |
| Gln | Trp | Thr | Ser | Lys | Thr | Ile | Ser | Arg | Phe | Trp | Asp | Lys | Gly | Phe | His |
| | | | 165 | | | | | 170 | | | | | 175 | | |
| Thr | Ile | Gly | Glu | Leu | Thr | Tyr | His | Ser | Ala | Asn | Tyr | Thr | Ala | Arg | Tyr |
| | | | 180 | | | | | 185 | | | | | 190 | | |
| Thr | Thr | Lys | Lys | Leu | Gly | Val | Lys | Asp | Tyr | Lys | Ala | Leu | Gln | Leu | Val |
| | | 195 | | | | | 200 | | | | | 205 | | | |
| Pro | Glu | Lys | Leu | Arg | Met | Ser | Lys | Gly | Ile | Gly | Leu | Lys | Tyr | Phe | Met |
| | 210 | | | | | 215 | | | | | 220 | | | | |
| Glu | Asn | Lys | Glu | Arg | Ile | Tyr | Lys | Glu | Asp | Ser | Val | Leu | Ile | Ser | Thr |
| 225 | | | | | 230 | | | | | 235 | | | | | 240 |
| Asp | Lys | Gly | Ile | Lys | Arg | Phe | Lys | Val | Pro | Lys | Tyr | Phe | Asp | Arg | Arg |
| | | | | 245 | | | | | 250 | | | | | 255 | |
| Met | Glu | Arg | Glu | Trp | Gln | Asp | Glu | Phe | Tyr | Leu | Asp | Tyr | Ile | Lys | Glu |
| | | | 260 | | | | | 265 | | | | | 270 | | |
| Lys | Arg | Glu | Lys | Val | Ala | Lys | Arg | Thr | Leu | Phe | Gln | Arg | Gln | Ile | Val |
| | | 275 | | | | | 280 | | | | | 285 | | | |
| Ser | Ser | Arg | Ser | Tyr | Thr | Asp | Tyr | Leu | Gly | Asp | Glu | Gln | Lys | Lys | Leu |
| | 290 | | | | | 295 | | | | | 300 | | | | |
| Asn | Asn | Ile | Val | Lys | Arg | Leu | Thr | Arg | Pro | Leu | Lys | Thr | Gly | Lys | Lys |
| 305 | | | | | 310 | | | | | 315 | | | | | 320 |

(2) INFORMATION FOR SEQ ID NO:18:

(i) SEQUENCE CHARACTERISTICS:
(A) LENGTH: 21 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:18:

```
Met  Ala  Lys  Gly  Arg  Lys  Leu  Pro  Ser  Val  Met  Lys  Asn  Arg  Phe  Ser
1                   5                        10                       15

Glu  Val  Pro  Thr  Ala
                    20
```

( 2 ) INFORMATION FOR SEQ ID NO:19:

( i ) SEQUENCE CHARACTERISTICS:
        ( A ) LENGTH: 21 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:19:

```
Met  Val  Arg  Asn  Arg  Arg  Leu  Pro  Ser  Val  Met  Ser  His  Ser  Phe  Ala
1                   5                        10                       15

Gln  Val  Pro  Ser  Ala
                    20
```

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:20:

```
Val  Arg  Asn  Arg  Arg  Leu  Pro  Ser  Val  Met  Ser  Xaa  Ser  Phe  Ala  Gln
1                   5                        10                       15

Val  Pro  Xaa  Ala
               20
```

( 2 ) INFORMATION FOR SEQ ID NO:21:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
ATGAAAGTTT  TTACAGTGTT  TGATATTAAG  ACGGAAATTT  ATCAGCAGCC  TTTTTTTATG    60

CAGGCTACGG  GAGCGGCAAT  CAGAGCGTTT  TCCGATATGG  TAAATGAGGA  TCCTTCGAAA   120

AATCAATTTG  CCGCGCATCC  TGAAGATTAC  ATTCTCTATG  AGATTGGATC  TTACGATGAC   180

TCTACTGGAA  ACTTCATTCC  CTTAGATGTG  CCTAAAGCCT  TAGGAACAGG  CTTGGATTTT   240

AAGCACAAAC  AGTAG                                                       255
```

( 2 ) INFORMATION FOR SEQ ID NO:22:

( i ) SEQUENCE CHARACTERISTICS:
        ( A ) LENGTH: 84 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:22:

-continued

| Met | Lys | Val | Phe | Thr | Val | Phe | Asp | Ile | Lys | Thr | Glu | Ile | Tyr | Gln | Gln |
| 1 | | | | 5 | | | | | 10 | | | | | 15 | |

| Pro | Phe | Phe | Met | Gln | Ala | Thr | Gly | Ala | Ala | Ile | Arg | Ala | Phe | Ser | Asp |
| | | | 20 | | | | | 25 | | | | | 30 | | |

| Met | Val | Asn | Glu | Asp | Pro | Ser | Lys | Asn | Gln | Phe | Ala | Ala | His | Pro | Glu |
| | | 35 | | | | | 40 | | | | | 45 | | | |

| Asp | Tyr | Ile | Leu | Tyr | Glu | Ile | Gly | Ser | Tyr | Asp | Asp | Ser | Thr | Gly | Asn |
| | 50 | | | | | 55 | | | | | 60 | | | | |

| Phe | Ile | Pro | Leu | Asp | Val | Pro | Lys | Ala | Leu | Gly | Thr | Gly | Leu | Asp | Phe |
| 65 | | | | | 70 | | | | | 75 | | | | | 80 |

| Lys | His | Lys | Gln |

( 2 ) INFORMATION FOR SEQ ID NO:23:

( i ) SEQUENCE CHARACTERISTICS:
        ( A ) LENGTH: 96 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:23:

| Met | His | Met | Phe | Tyr | Tyr | Ser | Ile | Tyr | Asp | Arg | Lys | Ala | Arg | Ser | Tyr |
| 1 | | | | 5 | | | | | 10 | | | | | 15 | |

| Gly | Asp | Leu | Ile | Ser | Phe | Pro | Ser | Gly | Glu | Lys | Glu | Ala | Ala | Ile | Arg |
| | | | 20 | | | | | 25 | | | | | 30 | | |

| Trp | Phe | Arg | Asp | Val | Val | Met | Asp | Ser | Asp | Ser | Lys | Asn | Ile | Leu | His |
| | | 35 | | | | | 40 | | | | | 45 | | | |

| Arg | Tyr | Pro | Glu | Asp | Phe | Asp | Phe | Cys | Tyr | Ile | Gly | Tyr | Phe | Asp | Lys |
| | | 50 | | | | | 55 | | | | | 60 | | | |

| Asp | Lys | Gly | Arg | Phe | Tyr | Pro | Val | Asp | Ala | Gly | Ile | Val | Thr | Ile | Ile |
| 65 | | | | | 70 | | | | | 75 | | | | | 80 |

| Asn | Ala | Gly | Glu | Phe | Phe | Leu | Asp | Ser | Glu | Tyr | Arg | Gln | Glu | Glu | Val |
| | | | | 85 | | | | | 90 | | | | | 95 | |

BACTERIOPHAGE OF *CHLAMYDIA PSITTACI*

The subject matter of this application was made with support from the United States Government (National Institute of Health Grant No. RO1 AI26280).

FIELD OF THE INVENTION

The present invention relates to an isolated bacteriophage, and more particularly to a bacteriophage designated φCPG1 of *Chlamydia psittaci* strain Guinea Pig Inclusion Conjunctivitis (GPIC), and uses of the bacteriophage.

BACKGROUND OF THE INVENTION

Chlamydia is a genus of gram-negative coccoidal bacteria which are obligate intracellular parasites. These pathogenic bacteria multiply only within the cytoplasm of vertebrate host cells by a developmental cycle that is unique among microorganisms. There are three stages in the cycle. The small infectious form of the microorganism first attaches itself to the host cell membrane and is engulfed by a process resembling phagocytosis. This small infectious form is called the elementary body (EB). A vacuole, derived from the host cell surface membranes, contains the EB and the EB is reorganized to form a larger body (called the reticulate body or RB). Within the membrane-bound vacuole (called the inclusion), the RB grows in size and divides repeatedly by binary fission. Numerous daughter cells are formed, and these again reorganize becoming small EBs. Eventually, the entire inclusion becomes filled with the small infectious particles (EBs). The EBs are then released after lysis of the cell, and can survive extracellularly to repeat the cycle and infect other healthy cells.

Chlamydiae produce cytopathology and are the etiologic agents of a variety of diseases of man and other animals. Strains of *C. trachomatis* cause well-known diseases of the ocular and urogenital tracts in humans (including trachoma, inclusion conjunctivitis, non-gonococcal urethritis, pelvic inflammatory disease, and lymphogranuloma venereum), and murine pneumonitis in mice. Strains of *C. psittaci* cause numerous diseases of man and animals, manifested primarily as pneumonitis, arthritis, placentitis (leading to abortion), and enteritis. *C. psittaci* causes psittacosis and ornithosis in wild and domestic birds, and psittacosis in man.

It has been estimated that 500 million people worldwide are affected by the ocular chronic disease trachoma, often referred to as the leading cause of preventable blindness. In the United States alone, it is estimated that more than four million individuals contact chlamydial sexually transmitted diseases (STDs) annually, and while no estimates are available worldwide, a conservative guess is that several hundred million people are infected. Thus, the magnitude of the Chlamydia problem in any given year is close to one billion or so infected people worldwide.

Psycho-socio-economic factors surrounding human management of chlamydial diseases and the unique chlamydial intracellular life cycle are two important causes of the magnitude of chlamydial disease. A further factor is the continuing inability of researchers to carry out genetic analysis of this organism. Although many chlamydial genes have now been cloned and characterized, it has not been possible to incorporate mutant or foreign genes into Chlamydia. As a result, functional characterization of cloned chlamydial genes is usually performed by analysis of sequence homology with genes from other, better characterized systems. The development of genetics for Chlamydia would constitute a major advance for many areas of Chlamydia research.

However, the development of methods of genetic transfer for Chlamydia presents unique challenges. One is that the most reasonable target for transformation, the metabolically active intracellular RB, is non-infectious. Therefore, the RB must be transformed while inside the chlamydial inclusion which itself resides inside the host cell. In other words, transforming DNA would have to go through four distinct membranes: the plasma membrane of the host cell, the inclusion membrane and the two membranes of the RB envelope. Transforming the metabolically dormant extracellular form, the EB, may alternatively be possible. However, rendering these small, spore-like particles competent for DNA uptake may also constitute a formidable task. Thus, a system which would facilitate both the uptake of foreign DNA by chlamydial cells and the subsequent replication and expression of this DNA within chlamydial cells is desirable.

In this regard, the use of bacteriophages as cloning vectors is a well established procedure for certain bacteria, such as *Escherichia coli*. The process known as transfection involves the use of a bacterial virus (or bacteriophage) to deliver DNA (contained in the virus) into the cell it infects. If the DNA molecule of the bacteriophage is "engineered" by manipulation of its sequence, and then intentionally introduced to a population of bacteria under conditions promoting transfection, the bacteria can be "genetically engineered" in a relatively simple process.

The application of these techniques to Chlamydia has not yet been shown. The only bacteriophage previously isolated from a chlamydial species is Chp1. Chp1 is a bacteriophage of avian *Chlamydia psittaci* (Richmond et al., FEMS Microbiology Letters 14:31–36 (1982); Storey et al., Journal of General Microbiology 70:3381–3390 (1989)), and is not capable of infecting mammalian Chlamydia.

A need continues to exists, therefore, for a means to genetically transfer mutant or foreign genes into Chlamydia, especially mammalian Chlamydia.

SUMMARY OF INVENTION

This need is met by the bacteriophage of the subject invention. The subject invention is directed to an isolated bacteriophage designated φCPG1, which can be used as a cloning vector, as well as to a cloning vector comprising packaged DNA of the bacteriophage φCPG1 and inserted heterologous DNA. The invention is further directed to an isolated DNA molecule encoding bacteriophage φCPG1 as well as to a DNA molecule comprising DNA encoding bacteriophage φCPG1 and heterologous DNA inserted into the DNA encoding the bacteriophage. The present invention also provides oligonucleotide sequences consisting essentially of a portion of a DNA molecule encoding bacteriophage φCPG1.

Intrinsic to the life cycle of bacteriophage φCPG1 described herein are steps for DNA uptake by, as well as replication and expression within, a chlamydial cell (including chlamydiae infecting mammalian cells). Thus the bacteriophage φCPG1 of the present invention allows for the genetic manipulation of chlamydial cells, with the benefits derived therefrom as discussed more fully below.

BRIEF DESCRIPTION OF THE DRAWINGS

These and other features and advantages of this invention will be evident from the following detailed description of preferred embodiments when read in conjunction with the accompanying drawings in which:

FIG. 1 illustrates the nucleotide sequence homology between ORF1 of φCPG1 and the VP1 gene of Chp1.

DETAILED DESCRIPTION

Figure 2:
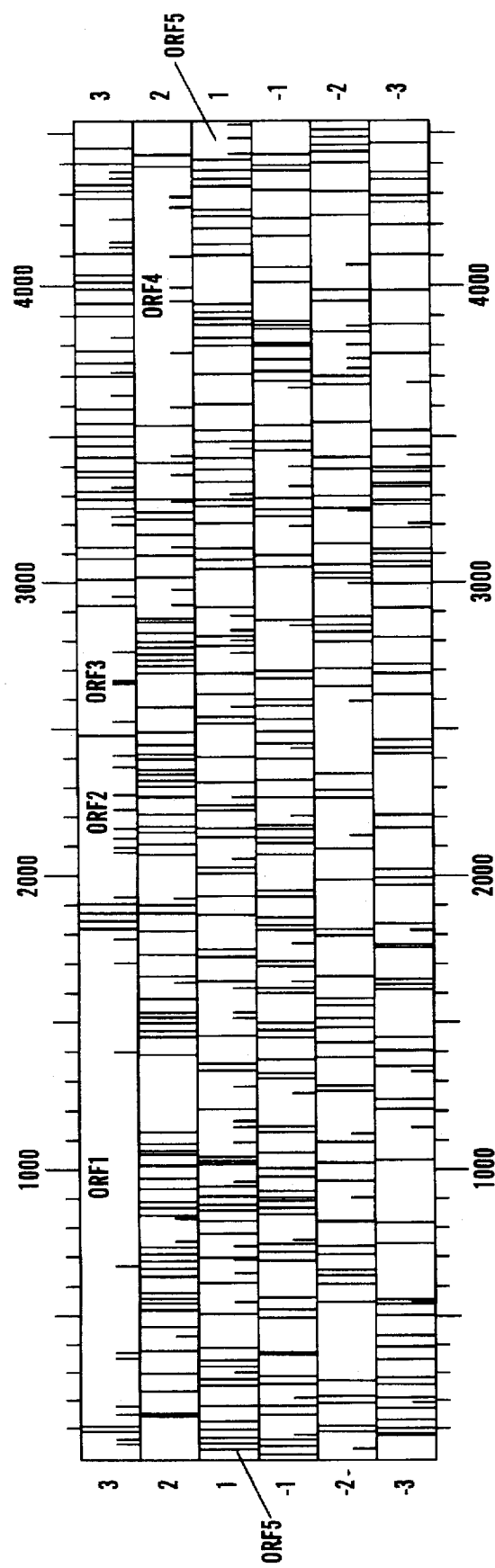
FIG. 2 is a physical map of the φCPG1 genome indicating all possible open reading frames. Vertical half bars represent all possible translational starts while full vertical bars represent all possible translational stops in each frame.

This invention relates to the bacteriophage φCPG1, per se; its genomic, or genetic component (DNA), entire and as fragments; and its derivatives (deletion and hybrid variants thereof) which are useful as shuttle cloning vectors for organisms such as Chlamydia. The resultant modified cells have utility through the imparting of valuable properties to the cells by virtue of the presence of foreign nucleic acid therein.

The invention provides an isolated bacteriophage designated φCPG1. This phage can be used to infect suitable cells, including mammalian Chlamydia such as the strain from which the vector was isolated, *Chlamydia psittaci* strain Guinea Pig Inclusion Conjunctivitis. Infection of suitable cells can be accomplished using methods well known in the art. One such method, for infection of eukaryotic cells, comprises simple mixing of a phage suspension with a phage-free Chlamydia inoculum prior to infection of host eukaryotic cells.

Antibodies can also be raised to the bacteriophage ϕCPG1, and to a portion or fragment of ϕCPG1. The portion or fragment can be encoded by the open reading frames ORF1 (as shown in nucleotide SEQ ID NO:2), ORF2 (as shown in nucleotide SEQ ID NO:3), ORF3 (as shown in nucleotide SEQ ID NO:4), ORF4 (as shown in nucleotide SEQ ID NO:5), or ORF 5 (as shown in nucleotide SEQ ID NO:21), for example. Antibodies of the subject invention include polyclonal antibodies and monoclonal antibodies which are capable of recognizing ϕCPG1 or portions thereof. It is known in the art that fragments of such antibodies can also be used to bind to the ϕCPG1 or portions thereof. These antibodies or fragments thereof can thus be used to detect the presence of ϕCPG1 in a sample, thereby indicating past or present infection of Chlamydia. An antibody directed to a homologous portion of ϕCPG1, i.e. homologous with other Chlamydia bacteriophage or "conserved" among Chlamydia bacteriophage, can be used to detect all Chlamydia bacteriophages. An antibody specific for ϕCPG1, i.e. not directed to a homologous or conserved portion, can be used to specifically detect ϕCPG1.

The invention further provides an isolated circular DNA molecule encoding bacteriophage ϕCPG1. The DNA molecule has a nucleotide sequence as shown SEQ ID NO:1, or a nucleotide sequence encoding amino acid sequences that are individually at least 95% identical to their counterpart amino acid sequences encoded by the ϕCPG1 genomic sequence as shown in SEQ ID NOs:6, 7, 8, 9, and 22.

The DNA molecule includes five significant open reading frames (ORFs). The ATG start codon for the first ORF, ORF1, is located at nucleotides 156–158 of SEQ ID NO:1, and the TAA stop codon for ORF1 is located at nucleotides 1815–1817. The ATG start codon for the second ORF, ORF2, is located at nucleotides 1923–1925 of SEQ ID NO:1, and the TAA stop codon for ORF2 is located at nucleotides 2481–2483. The ATG start codon for the third ORF, ORF3, is located at nucleotides 2484–2486 of SEQ ID NO:1, and the TGA stop codon for ORF3 is located at nucleotides 2928–2930. The ATG start codon for the fourth ORF, ORF4, is located at nucleotide 3602–3604 of SEQ ID NO:1, and the TAG stop codon for ORF4 is located at nucleotides 4391–4393. The ATG start codon for the fifth ORF, ORF5, is located at nucleotide 4526–4528 of SEQ ID NO:1, and the TAG stop codon for ORF5 is located at nucleotide 146–148. Referring to SEQ ID NO:1, ORF1 thus extends from nucleotide 156 to nucleotide 1817; ORF2 extends from nucleotide 1923 to nucleotide 2483; ORF3 extends from nucleotide 2484 to nucleotide 2930; ORF4 extends from nucleotide 3602 to nucleotide 4393; and ORF5 extends from nucleotide 4526 to nucleotide 148 (the DNA is circular).

The invention further provides for fragments of the isolated DNA molecule encoding bacteriophage ϕCPG1. ORF1, ORF2, ORF3, ORF4 and ORF5 are examples of such fragments. Additional desirable fragments may be identified by identifying nucleotide regions homologous among various Chlamydia bacteriophages. A fragment which "consists essentially" of, for example, ORF1, has as an essential part of the fragment a nucleotide sequence encoding an amino acid sequence that is at least 95% identical to the amino acid sequence of ORF1 (SEQ ID NO:6). Non-essential nucleotides could be placed at the 5' and/or 3' end of the fragment without affecting the properties of the essential nucleotide sequence. A fragment refers to a continuous portion of the DNA molecule that is less than the entire molecule. As used herein, a nucleic acid molecule encoding ϕCPG1 has a nucleotide sequence encoding amino acid sequences that are individually at least 95% identical to their counterpart amino acid sequences encoded by the ϕCPG1 genomic sequence as shown in SEQ ID NOs:6, 7, 8, 9 and 22. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved). It is also possible to have minor nucleotide and/or amino acid additions, deletions, and/or substitutions in the sequence encoding ϕCPG1 and to still have a DNA molecule encoding a functional bacteriophage ϕCPG1.

This DNA molecule can theoretically be introduced into chlamydial cells directly. The standard methods for introducing DNA into a host cell (i.e. for transforming the host cell) include microinjection, calcium phosphate cotransfection, electroporation, and liposome fusion. However, the most efficient method for introducing the bacteriophage ϕCPG1 DNA into the chlamydial cells is by utilizing the bacteriophage itself to naturally infect the chlamydial cells.

Bacteriophage ϕCPG1 DNA can be reproduced by utilizing a cloning vector into which the DNA molecule encoding bacteriophage ϕCPG1 is placed. In one embodiment, the phage DNA may be included or inserted into a plasmid, such as plasmid pϕCPG1-B (which is a plasmid with bacteriophage ϕCPG1 DNA inserted therein).

U.S. Pat. No. 4,237,224 to Cohen and Boyer, which is hereby incorporated by reference, describes the production of recombinant plasmids using restriction enzyme cleavage and ligation with DNA ligase. These recombinant plasmids are then introduced into host cells by means of transformation and the DNA of the plasmid (now including the phage DNA with or without DNA heterologous to the phage DNA) is replicated in unicellular cultures including procaryotic organisms such as *E. coli.*

The bacteriophage DNA sequences are cloned into the expression vector, or the heterologous DNA is cloned into the bacteriophage DNA, using standard cloning procedures in the art, as described by Sambrook et al., Molecular Cloning: A Laboratory Manual, 2d Edition, Cold Spring Harbor Laboratory Press, Cold Spring Harbor, N.Y. (1989), which is hereby incorporated by reference.

Further provided is a DNA molecule comprising DNA encoding bacteriophage φCPG1 and heterologous DNA inserted into the DNA encoding the bacteriophage. As used throughout this application, "heterologous" refers to DNA not normally present, i.e., foreign DNA to the bacteriophage φCPG1 DNA. The heterologous DNA may be inserted into the DNA encoding bacteriophage φCPG1 at the site of a deletion within the phage DNA.

This DNA molecule (comprising DNA encoding bacteriophage φCPG1 with heterologous DNA inserted therein) can be utilized to transform cells, including chlamydial cells.

A DNA molecule encoding bacteriophage φCPG1, with or without inserted heterologous DNA, can be incorporated in cells using conventional recombinant DNA technology. Naked DNA can be inserted into a cell via techniques such as conjugation, transduction, microinjection, chemically-mediated transfection, microprojectile-mediated transformation, electroporation, and liposome fusion.

The invention also provides oligonucleotides consisting essentially of a portion of the DNA molecule encoding bacteriophage φCPG1. The portion of the DNA molecule is similar to a fragment, and can be ORF1, ORF2, ORF3, ORF4, ORF5, or smaller homologous portions of the DNA molecule (homologous to other Chlamydia bacteriophages). These oligonucleotides can be utilized to detect DNA homologous thereto in a sample, by contacting the sample with a labeled oligonucleotide under conditions suitable for hybridization of the oligonucleotide to complementary homologous DNA within the sample. The resulting hybridized DNA is detected, thereby detecting the presence of homologous DNA in the sample.

In a further embodiment of the present invention, the oligonucleotide consists essentially of a portion of the DNA molecule encoding bacteriophage φCPG1, the portion being homologous to a portion of DNA of other chlamydial bacteriophages. This enables the oligonucleotide to be utilized as a probe to detect other chlamydial phages.

In a further aspect of the present invention, the polymerase chain reaction (PCR) technique can be utilized to amplify a specified DNA sequence. PCR is described in detail in U.S. Pat. Nos. 4,683,195, issued Jul. 28, 1987, 4,683,202, issued Jul. 28, 1987, 4,800,159, issued Jan. 24, 1989, and 4,965,188, issued Oct. 23, 1990, all of Mullis et al. The contents of each of these patents are hereby incorporated by reference. Such a technique is useful when portions of the DNA sequence encoding the bacteriophage are utilized as primers and probes to detect homologous portions of DNA in a sample. For example, DNA primer sequences selected from within a homologous sequence are used in the PCR technique to amplify the homologous sequence. A DNA probe sequence, also part of the homologous sequence, is then utilized to detect the amplified sequence. This can be done by conventional hybridization techniques, wherein the probe sequence is labeled and can be detected after hybridizing with the homologous sequence within a sample.

EXAMPLES

The following examples illustrate, but are not intended to limit, the present invention.

Example 1

A bacteriophage identified as φCPG1, capable of infecting *Chlamydia psittaci* strain Guinea Pig Inclusion Conjunctivitis (GPIC), and the complete nucleotide sequence of its DNA (as shown in SEQ ID NO:1) and predicted translation products are disclosed. φCPG1 is related to Chp1, a previously isolated bacteriophage of avian *Chlamydia psittaci* (Richmond et al., FEMS Microbiology Letters 14:31–36 (1982); Storey et al., Journal of General Microbiology 70:3381–3390 (1989)), to SPV4, an isometric virus which infects the helical mollicute *Spiroplasma melliferum* (Renaudin et al., Journal of Bacteriology 169:4950–4961. (1987)), and to a lesser degree to bacteriophage φX174 and other members of the Microviridae. φCPG1 is capable of lytic growth, in the process killing the chlamydiae that it infects.

Example 2

φCPG1, a bacteriophage infecting *Chlamydia psittaci* strain GPIC, was identified by homology to a previously characterized Chlamydia bacteriophage of avian *C. psittaci* named Chp1 (Richmond et al. 1982).

φCPG1 presents several inherent advantages over Chp1:

(a) since it infects a mammalian Chlamydia (GPIC), φCPG1 has a different host range than Chp1 which only infects avian strains;

(b) φCPG1 infects GPIC, a *C. psittaci* strain whose genital and ocular infection in the guinea pig provide useful animal models for human disease;

(c) φCPG1 is the second Chlamydia bacteriophage to be obtained, for which a recombinant chimeric plasmid carrying φCPG1 DNA has been isolated and maintained in *Escherichia coli*. A comparison of the nucleotide sequence of the φCPG1 genome with that of Chp1 reveals regions of substantial sequence homology and regions of divergence. Moreover, both φCPG1 and Chp1 display significant homology with SPV4, a virus infecting *Spiroplasma melliferum*. Thus it is possible, using PCR and primers derived from the conserved regions, to screen human clinical specimens for the presence of homologous phages.

Example 3

The isolation of φCPG1 and the subsequent molecular cloning of its DNA have important short and long term implications for Chlamydia research. The particular significance of φCPG1 is that, for the first time, a vector for the introduction of foreign DNA into a mammalian Chlamydia is available. In general, four broad categories for the use of such a bacteriophage- or bacteriophage DNA-based system of genetic transfer are: (1) the development of Chlamydia vaccines, (2) the development of diagnostic tests for chlamydial infections, (3) the development of tools to study the epidemiology of chlamydial infections, and (4) the development of therapeutic reagents and therapeutic strategies against chlamydial infections of humans and animals.

Since φCPG1 is the second phage discovered which infects bacteria of the genus Chlamydia, a direct comparison of the nucleotide sequences of, for instance, the first open reading frame of the φCPG1 bacteriophage genome (ORF1) with the first open reading frame of the Chp1 bacteriophage genome (Chp1 VP1) identifies segments of high homology and segments which are variable (see FIG. 1 in which SEQ ID NO:2 represents the nucleotide sequence of ORF1 of φCPG1 and SEQ ID NO:10 represents the nucleotide sequence of VP1 of Chp1). The sequence of homologous DNA segments which are identified can be used to probe for other homologous phage DNAs in other strains. For example, this can be accomplished using oligonucleotide primers derived from the homologous segments of ORF1 and subsequent PCR amplification of specimens known or suspected to include Chlamydia or Chlamydia-related bacteria (e.g. cervical swabs for *C. trachomatis* bacteria). The discovery of new bacteriophages in other Chlamydia strains would make all developments described here applicable to other Chlamydia species including the human pathogens *C. trachomatis* and *C. pneumonias*, other strains of *C. psittaci*, and *C. pecorum*. Furthermore, since the Chlamydia bacteriophages display significant homology to SPV4, a bacteriophage of *Spiroplasma melliferum*, a similar approach may be taken to isolate φCPG1-related phages from a wide range of bacterial species.

Example 4

The discovery of a Chlamydia bacteriophage supplies a convenient tool for the development of a method to introduce DNA into Chlamydia bacteria. Many possibilities exist. The following examples are but three among these.

1. naked bacteriophage DNA may be used, in whole or in part, as part of a shuttle system whereby DNA, of chlamydial or foreign origin, modified or not, may be introduced into chlamydial cells;
2. naked bacteriophage DNA, in whole or in part, may be modified (e.g., to include a transposable element, a drug resistance gene, a modified chlamydial gene, etc.) and packaged in vitro with purified components or using a recombinant system to generate "infectious phage" particles. The natural route of bacteriophage infection may then be used to deliver the DNA into chlamydial cells; and
3. recombinant bacteriophage DNA may be modified and expressed in a suitable microbial host so as to produce infectious bacteriophage particles. The normal route of bacteriophage infection may then be used to deliver the DNA into chlamydial cells.

The development of a genetic system for Chlamydia species is of paramount importance for the study of these organisms. In particular, this methodology, including the ability to produce mutant Chlamydia strains, would have a profound impact in the understanding of the molecular mechanisms which underlie the ability of these organisms to cause disease in humans and animals. Since φCPG1 is a parasite of *C. psittaci* GPIC, this would allow the direct testing of mutants in the guinea pig:GPIC model system for human chlamydial diseases.

Example 5

The impact in vaccine development may be several fold. For example, using a φCPG1-based genetic transfer system, mutant Chlamydia strains may be constructed which will be attenuated in the human or animal host with respect to infectivity or virulence. Such strains would ideally remain highly immunogenic so as to elicit protective immunity in the vaccinated host, yet would not cause the immunopathology normally associated with chlamydial infections (e.g. conjunctival scarring leading to blindness, tubal scarring leading to ectopic pregnancy or infertility in women, etc.). Attenuated mutant strains of Chlamydia may be constructed by allelic exchange targeting genetic determinants that are essential for disease pathology but are dispensable for growth.

An approach may involve the genetic modification of determinants involved in pathogenesis. These include genes encoding adherence and invasion properties of chlamydial elementary bodies. Since it has been demonstrated that chlamydiae may enter into susceptible eukaryotic cells by multiple pathways, the genetic inactivation of any one of these pathways may render the bacteria less "virulent" in the infected host, e.g. by attenuating the overall infection or by preventing extensive spreading of the infection. This, in turn, may dramatically reduce the morbidity associated with chronic chlamydial infections and make such mutant strains of Chlamydia useful as live vaccines.

An alternative approach may involve the modification of genes that are required for intracellular growth in vivo, but do not prevent maintenance and growth of Chlamydia in vitro. Thus a metabolite, which is required by the mutant, can be provided in vitro but would not be available in the infected host. Such in vitro grown chlamydiae would be expected to cause a limited infection in the host, without disease symptoms. However, the infection may be sufficient to elicit immune responses which may be protective against subsequent infections by wild type strains. A precedent of such a live vaccine system exists with various *Salmonella typhimurium* mutant strains which are avirulent, yet elicit anti-Salmonella responses which are usually sufficient for immune protection.

A variety of other approaches using a bacteriophage-based genetic system may help to identify "protective" antigens which can be used as components of a Chlamydia vaccine.

Example 6

Bacteriophage particles or components thereof, either from recombinant origin or reconstituted in vitro, may themselves bind Chlamydia bacteria with high affinity and high specificity. This in turn may provide the basis for the design of highly specific probes for the detection of Chlamydia bacteria in various clinical and environmental sources.

The analysis by serology of the immune response of the infected host to bacteriophage components may provide a reliable diagnostic test of chlamydial infections. Antibodies to the ORF1 gene product or other bacteriophage components could be detected using a variety of immunological assays including ELISAs, radioimmunoassays or more traditional techniques. Assuming that bacteriophage infection of Chlamydia is widespread, detection of anti-bacteriophage antibodies in the serum of patients would possibly constitute diagnostic evidence of current or past chlamydial infection.

Moreover, since phage infection may contribute to Chlamydia disease pathology, early detection of phage presence, directly or serologically, may constitute an important prediction tool for disease outcome for the physician.

Example 7

In a broad sense, the methodologies envisioned above should enhance our understanding of Chlamydia biology and pathogenesis and, as a direct consequence, should enhance our ability to prevent and fight Chlamydia-caused diseases. Since mutant analysis may allow one to identify essential physiological and virulence determinants and to characterize how the expression of these determinants is regulated, it will be possible, for example, to target specific chlamydial molecules with synthetic or recombinant inhibitors based on the critical role of the target molecules in intracellular growth or virulence.

The study of the bacteriophage interaction with the Chlamydia cell may also provide a direct means of therapeutic intervention. Since the bacteriophage causes a lytic infection of Chlamydia cells, it should "attenuate" the chlamydial infection (i.e., reduce the infectious load) of eukaryotic cells. Moreover, the virulence of the bacteriophage toward Chlamydia could also be enhanced (e.g. by selecting or screening for more infectious phages). Treatment of other bacterial infections with lyric bacteriophages has been attempted in other systems with little success. However, the containment of chlamydial infections within defined anatomical sites that are readily accessible to external treatment (e.g. the conjunctiva or the genital tract) may render bacteriophage treatment of chlamydial infections possible. In this case, a bacteriophage suspension may be inoculated in the appropriate site in order to infect and lyse the infecting chlamydiae. Such a treatment may entirely eliminate the chlamydial infection or alternatively reduce its magnitude, thereby eliminating or reducing associated morbidity.

Alternatively, bacteriophage components may competitively inhibit chlamydial adherence to or entry into susceptible eukaryotic cells thereby blocking chlamydial infection. Thus, the study of the phage biology itself and of its interaction with the host chlamydial cell may lead to the development of new bacteriophage-derived therapies which may directly inhibit, attenuate or suppress chlamydial infectivity. In this case, bacteriophage-derived peptides or proteins may be effective as therapeutic agents by blocking the specific interaction(s) between eukaryotic receptors and their chlamydial ligands which are normally used by chlamydial elementary bodies to gain entry into the eukaryotic cell.

Example 8

The existence of the bacteriophage φCPG1, which infects *Chlamydia psittaci* strain GPIC, was demonstrated by the following experiments:

a) a polypeptide of apparent molecular weight 65,000 gradually came to prominence in purified EB preparations. A φCPG1 major protein of apparent molecular weight 65,000, which is homologous to VP1 of Chp1 and to VG1 of SPV4, was found in φCPG1-infected purified GPIC elementary body proteins. N-terminal sequence analysis was performed on the gel-purified polypeptide. The 18 amino acid residue sequence obtained displayed 56% homology with the predicted amino terminal sequence of a structural protein (VP1) of a previously characterized single-stranded DNA bacteriophage named Chp1, which infects avian *Chlamydia psittaci*. SEQ ID NO:18 is the amino terminal sequence of VP1 of bacteriophage Chp1. The amino terminal sequence of the VP1 homolog of φCPG1 predicted from the nucleotide sequence is as shown in SEQ ID NO:19, and the determined amino terminal sequence of the VP1 homolog of φCPG1 is as shown in SEQ ID NO:20. The amino acid identity between these three sequences is shown in Table 1.

TABLE 1

| RESIDUE NO. | SEQ ID NO. | IDENTICAL TO: RESIDUE NO. | SEQ NO. | IDENTICAL TO: RESIDUE NO. | SEQ NO. |
|---|---|---|---|---|---|
| 1 | 18 | 1 | 19 | — | — |
| 5 | 18 | 5 | 19 | 4 | 20 |
| 7–11 | 18 | 7–11 | 19 | 6–10 | 20 |
| 15 | 18 | 15 | 19 | 14 | 20 |
| 18 and 19 | 18 | 18 and 19 | 19 | 17 and 18 | 20 |
| 21 | 18 | 21 | 19 | 20 | 20 | b) φCPG1 virions were visualized by electron microscopy. Briefly, φCPG1-infected GPIC cultures were negatively stained or fixed and thin sectioned and prepared for electron microscopy. φCPG1 phage particles ultrastructurally similar to Chp1 were observed free or in association with chlamydial cells and cell envelopes, inside and outside of chlamydial intracellular inclusions.

c) Partial nucleotide sequence of cloned φCPG1 DNA revealed an open reading frame which upon translation was identical to the determined 18 N-terminal amino acid sequence of the 65 kiloDalton polypeptide (see above) and was 53.9% identical and 69.6% similar to the VP1 structural protein of Chp1 over the whole length. SEQ ID NO:6 shows the predicted amino acid sequence of the translation product of ORF1 of the φCPG1 genome, and SEQ ID NOS:11 and 12 show the amino acid sequences of the homologous counterparts from Chp1 and SPV4, respectively.

Example 9

The molecular cloning of φCPG1 genomic DNA was performed as follows. φCPG1 bacteriophage was enriched from a cleared lysate of HeLa cells infected with φCPG1-infected *C. psittaci* strain GPIC, then treated with proteinase K, and then single-stranded φCPG1 DNA was purified. Following second strand synthesis using random hexamer priming, φCPG1 DNA was ligated as a single 4.5 kilobase BamH1 fragment in pKS, generating plasmid pφCPG1-B. Nucleotide sequence analysis of the BamH1 insert of plasmid pφCPG1-B has revealed significant homology to Chp1 DNA, confirming that this chimeric DNA carries φCPG1 genomic DNA. Furthermore, sequence analysis of a PCR-generated fragment including the BamH1 site demonstrated that the BamH1 insert of pφCPG1-B represents the totality of the φCPG1 genome. A physical map of the pφCPG1-B insert indicating all open reading frames is shown in FIG. 2. Vertical half bars represent all possible translational starts while full vertical bars represent all possible translational stops in each frame.

Example 10

The complete nucleotide sequence of the pφCPG1-B BamH1 insert is shown in SEQ ID NO:1.

A comparative analysis with Chp1 DNA reveals that the general genetic organization is conserved. Significant nucleotide sequence homology is observed within ORF1 (FIG. 1) and within ORF2, ORF3, ORF4, and ORF5. When φCPG1 predicted translation products are compared with Chp1 products (VP1–VP3, ORF4, ORF5), different levels of homology are observed. These results confirm the evolutionary relationship between φCPG1 and Chp1 and justify the placement of φCPG1 in the family Microviridae, genus *Chlamydiamicrovirus* (see Virus Taxonomy, Murphy et al., eds., Springer-Verlag, New York (1995)).

A comparison of the φCPG1 genome with that of SPV4 also reveals homology for three putative translation products (ORF1/VG1, ORF2/VG4 and ORF4/VG2). However the general genetic organization is different and homology is not found for ORF3 of φCPG1 or for VG3 of SPV4. SEQ ID NO:6 represents the amino acid sequence of φCPG1 ORF1, which can be compared to SEQ ID NO:11 which is the amino acid sequence of Chp1 VP1 and to SEQ ID NO:12 which is the amino acid sequence of SPV4 VG1. SEQ ID NO:7 represents the amino acid sequence of φCPG1 ORF2, which can be compared to SEQ ID NO:13 which is the amino acid sequence of Chp1 VP2 and to SEQ ID NO:14 which is the amino acid sequence of SPV4 VG4. SEQ ID NO:8 is the amino acid sequence of φCPG1 ORF3, which can be compared to SEQ ID NO:15 which is the amino acid sequence of Chp1 VP3. SEQ ID NO:9 is the amino acid sequence of φCPG1 ORF4, which can be compared to SEQ ID NO:16 which is the amino acid sequence of Chp1 ORF4 and to SEQ ID NO:17 which is the amino acid sequence of SPV4 VG2. SEQ ID NO:22 is the amino acid sequence of φCPG1 ORF5, which can be compared to SEQ ID NO:23 which is the amino acid sequence of Chp1 ORF5.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. An isolated DNA molecule comprising the genomic sequence of bacteriophage φCPG1, said genomic sequence as shown in SEQ ID NO:1.

2. A fragment of the isolated DNA molecule of claim 1 wherein said fragment is selected from the group consisting of: a fragment consisting of nucleotides 156–1817 as shown in SEQ ID NO:1, a fragment consisting of nucleotides 1923–2483 as shown in SEQ ID NO:1, a fragment consisting of nucleotides 2484–2930 as shown in SEQ ID NO:1, a fragment consisting of nucleotides 3602–4393 as shown in SEQ ID NO:1, and a fragment consisting of nucleotides 4526–148 as shown in SEQ ID NO:1.

3. A cell comprising the DNA molecule of claim 1.

4. The cell of claim 3 wherein the cell is a Chlamydia cell.

5. The cell of claim 4 wherein the Chlamydia cell is a Chlamydia cell capable of infecting a mammalian cell.

6. The cell of claim 3 wherein the cell is an *Escherichia coli* cell.

7. A cloning vector comprising the DNA molecule of claim 1.

8. The cloning vector of claim 7 wherein the cloning vector comprises a bacteriophage.

9. The cloning vector of claim 7 wherein the cloning vector comprises a plasmid.

10. A cell comprising the cloning vector of claim 7.

11. The cell of claim 10 wherein the cell is an *Escherichia coli* cell.

12. An isolated DNA molecule comprising the genomic sequence of bacteriophage φCPG1, said genomic sequence including a nucleotide sequence encoding a first amino acid sequence at least 95% identical to SEQ ID NO:6, a second amino acid sequence at least 95% identical to SEQ ID NO:7, a third amino acid sequence at least 95% identical to SEQ ID NO:8, a fourth amino acid sequence at least 95% identical to SEQ ID NO:9, and a fifth amino acid sequence at least 95% identical to SEQ ID NO:22.

13. An isolated DNA molecule comprising the genomic sequence of bacteriophage φCPG1, said genomic sequence including a nucleotide sequence encoding a first amino acid sequence identical to SEQ ID NO:6, a second amino acid sequence identical to SEQ ID NO:7, a third amino acid sequence identical to SEQ ID NO:8, a fourth amino acid sequence identical to SEQ ID NO:9, and a fifth amino acid sequence identical to SEQ ID NO:22.

* * * * *